_US006086891A_

United States Patent [19]
Hurwitz et al.

[11] Patent Number: 6,086,891
[45] Date of Patent: Jul. 11, 2000

[54] BI-FUNCTIONAL PLASMID THAT CAN ACT AS BOTH A DNA VACCINE AND A RECOMBINANT VIRUS VECTOR

[75] Inventors: Julia Hurwitz; Christopher Coleclough, both of Germantown, Tenn.

[73] Assignee: St. Jude Children's Research Hospital, Memphis, Tenn.

[21] Appl. No.: 09/157,963

[22] Filed: Sep. 21, 1998

Related U.S. Application Data

[60] Division of application No. 08/788,815, Jan. 23, 1997, Pat. No. 5,846,546, which is a continuation-in-part of application No. 08/590,288, Jan. 23, 1996, Pat. No. 5,741,492.

[51] Int. Cl.[7] .................. A61K 39/21; A61K 39/245; C07H 21/02
[52] U.S. Cl. .................. 424/208.1; 424/230.1; 536/23.1
[58] Field of Search .............. 424/208.1, 230.1; 536/23.1

[56] References Cited

U.S. PATENT DOCUMENTS

| 5,081,226 | 1/1992 | Berzofsky et al. | 424/199.1 |
|---|---|---|---|
| 5,169,763 | 12/1992 | Kieny et al. | 424/199.1 |
| 5,198,214 | 3/1993 | Stolle et al. | 424/92 |

FOREIGN PATENT DOCUMENTS

| 2181435 | 4/1987 | United Kingdom . |
| WO 87/06262 | 10/1987 | WIPO . |
| WO 90/12880 | 11/1990 | WIPO . |
| WO 92/22641 | 12/1992 | WIPO . |
| WO 93/19183 | 9/1993 | WIPO . |
| WO 95/20660 | 8/1995 | WIPO . |

OTHER PUBLICATIONS

Hurwitz et al. (1997) Conf. Adv. Vacc. Dev., NIH, Bethesda, Poster 11.
Gritz et al. (1990) J. Virol. 64:5948–57.
Perales et al. (1995) J. AIDS & Human Retrovirol. 10:27–35.
Rencher et al. (1995) AIDS Res. Human Retroviruses 11:1131–3.
Ruby et al. (1990) Immun. Cell Biol. 68:113–7.
Fahey et al. (1992) Clin. Exp. Immunol. 88:1–5.
Fox, J.L. (1994) Bio/Tech. 12:128.
Hird et al. (1990) Immunotherapy with Monoclonal Antibodies, Genes and Cancer, Carney et al., Ed., pp. 183–189.
Berman et al. (1990) Nature 345:622–5.
Stephens et al. (1992) J. Gen. Virol. 73:1099–106.
Dallo et al. (1989) Virol. 173:323–9.
Belshe et al. (1994) J. Am. Med. Asso. 272:431.
Burns et al. (1994) Curr. Top. Microbiol. Immunol. 188:185–219.
Chakrabarti et al. (1985) Mol. Cell. Biol. 5:3403–9.
Cohen, J. (1994) Science 264:1072–4.
Cooney et al. (1993) Proc. Natl. Acad. Sci. USA 90:1882–6.
D'Hondt, E. (1992) Vaccine 10:s48–52.
Enami et al. (1991) J. Virol. 65:2711–3.
Enami et al. (1990) Proc. Natl. Acad. Sci. USA 87:3802–5.
Gorse, G.J. (1994) AIDS Res. Human Retroviruses 10:s141–3.
Graham et al. (1993) J. Inf. Dis. 167:533–7.
Graham et al. (1992) J. Inf. Dis. 166:244–52.

(List continued on next page.)

*Primary Examiner*—Hankyel Park
*Attorney, Agent, or Firm*—Klauber & Jackson

[57] ABSTRACT

Polyenv vaccines are provided that comprise mixtures of at least 4 to about 10,000 different recombinant viruses that each express a different HIV env variant or a portion thereof containing both constant and variable regions, as well as methods of making and using such polyenv vaccines and viruses, including the use of the polyenv vaccine, in live, attenuated or inactivated form, for prophylaxis or treatment of HIV infection. The viral vaccines of the invention are optimally combined with a recombinant HIV env booster, or a recombinant HIV env gene DNA priming or boosting vaccine.

24 Claims, 7 Drawing Sheets

OTHER PUBLICATIONS

Grunwald–Beard et al. (1991) J. Cancer Res. Clin. Oncol. 117:561–7.
Hallenberger et al. (1993) Virol. 193:510–4.
Ito et al. (1991) J. Virol. 65:5491–8.
Javaherian et al. (1989) Proc. Natl. Acad. Sci. USA 86:6768–72.
Keefer et al. (1994) AIDS Res. Human Retroviruses:s139–40.
Kilpatrick et al. (1987) J. Biol. Chem. 262:16116–21.
McElrath et al. (1994) J. Inf. Dis. 169:41–7.
Richman, D.D. (1994) AIDS Res. Human Retroviruses 10:901–5.
Richman, D.D. (1993) Antimirob. Agents Chemother. 37:1207–13.
Richman, D.D. (1992) AIDS Res. Human Retroviruses 8:1065–71.
Starcich et al. (1986) Cell 45:637–48.
Zagury et al. (1988) Nature 332:728–31.
Elchberg, J.W. (1991) Int. Conf. AIDS 7:88 Abstract F.A.2.
Girard et al. (1989) Int. Conf. AIDS 5:541 Abstract Th.C.O.47.
Enders et al. (1946) J. Immun. 54:283–91.
Enders et al. (1945) J. Exp. Med. 81:93–117.
Hilleman et al. (1967) New Eng. J. Med. 276:252–8.
Andersson et al., *J. Infect. Dis.* 174:977–85 (1996).
Fauci, *Science* 264:1072–1073 (May 1994).
Fenyo et al., *AIDS* 10:S97–S106 (1996).
Fries et al. *Vaccine* 14:428–34 (1996).
Gonczol et al., *Vaccine* 13:1080–5 (1995).
Hu et al., *Nature* 328:721–723 (1987).
Girard et al., *Int. Conf. AIDS* 5:541 (1989).
Lockey et al., *Aids Res Hum Retroviruses* 12:1297–1299 (1996).
Montefiori et al., *Journal of Infectious diseases* 173:60–67 (1996).
Moore and Ho, *AIDS* 9:S117–S136 (1995).
Moore, *Nature* 376:115 (1995).
Pialoux et al., *AIDS Res. Hum. Retroviruses* 11:373–81 (1995).
Pialoux et al, *erratum in AIDS Res. Hum. Retroviruses* 11:875 (1995).
Ratner et al., *Nature* 313:277–284 (1985).
Raz et al., *Proc. Natl. Acad. Sci.*, 91:9519–9523 (1994).
Steele, *Journal of NIH research* 6:40–42 (1994).
Ulmer et al., *Science*, 259:1745–1749 (1993).
Wang et al., *Proc. Natl. Acad. Sci.*, 90:4156–4160 (1993).
Xiang et al., *Virology* 219:220–7 (1996).
Neurath et al. (1991) AIDS Res. Hum. Retroviruses 7:813–23.
Lederle Lab. Dvi., Am. Cyanamid Com., Pneumococcal Vaccine Polyvalent PNU–IMUNE 23.
Shapiro et al. (1991) New Eng. J. Med. 325:1453–60.

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

AGCAGAAGAC AGTGGCAATG AGAGTGA      27

(2) INFORMATION FOR SEQ ID NO:2:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

CCACTCCATC CAGGTCATGT TATTCCAAAT                                                        30

(2) INFORMATION FOR SEQ ID NO:3:

(i) SEQUENCE CHARACTERISTICS:
               (A) LENGTH: 32 base pairs
               (B) TYPE: nucleic acid
               (C) STRANDEDNESS: single
               (D) TOPOLOGY: linear (ii) MOLECULE TYPE: cDNA (xi) SEQUENCE DESCRIPTION: SEQ ID NO:3:

GTGGGTCACA GTCTATTATG GGGTACCTGT GT                                                     32

(2) INFORMATION FOR SEQ ID NO:4:

(i) SEQUENCE CHARACTERISTICS:
               (A) LENGTH: 34 base pairs
               (B) TYPE: nucleic acid
               (C) STRANDEDNESS: single
               (D) TOPOLOGY: linear (ii) MOLECULE TYPE: cDNA (xi) SEQUENCE DESCRIPTION: SEQ ID NO:4:

CCAGAGATTT ATTACTCCAA CTAGCATTCC AAGG                                                   34

(2) INFORMATION FOR SEQ ID NO:5:

(i) SEQUENCE CHARACTERISTICS:
               (A) LENGTH: 28 base pairs
               (B) TYPE: nucleic acid
               (C) STRANDEDNESS: single
               (D) TOPOLOGY: linear (ii) MOLECULE TYPE: cDNA (xi) SEQUENCE DESCRIPTION: SEQ ID NO:5:

CCATGTGTAA AATTAACCCC ACTCTGTG                                                          28

(2) INFORMATION FOR SEQ ID NO:6:

(i) SEQUENCE CHARACTERISTICS:
               (A) LENGTH: 26 base pairs
               (B) TYPE: nucleic acid
               (C) STRANDEDNESS: single
               (D) TOPOLOGY: linear (ii) MOLECULE TYPE: cDNA (xi) SEQUENCE DESCRIPTION: SEQ ID NO:6:

TACAATTTCT GGGTCCCCTC CTGAGG                                                            26

(2) INFORMATION FOR SEQ ID NO:7:

(i) SEQUENCE CHARACTERISTICS:
               (A) LENGTH: 880 amino acids
               (B) TYPE: amino acid
               (C) STRANDEDNESS: both
               (D) TOPOLOGY: both (ii) MOLECULE TYPE: protein (xi) SEQUENCE DESCRIPTION: SEQ ID NO:7:

-continued

```
Lys Glu Gln Lys Thr Val Ala Met Arg Val Lys Glu Ser Gln Met Lys
 1               5                  10                  15
Lys Gln His Leu Trp Arg Trp Gly Trp Arg Trp Gly Thr Met Leu Leu
                20                  25                  30
Gly Leu Met Ile Cys Ser Ala Thr Glu Lys Leu Trp Val Thr Val Tyr
                35                  40                  45
Tyr Gly Val Pro Val Trp Lys Glu Ala Thr Thr Thr Leu Phe Cys Ala
 50                  55                  60
Ser Asp Ala Lys Ala Tyr Asp Thr Glu Val His Asn Val Trp Ala Thr
 65                  70                  75                  80
His Ala Cys Val Pro Thr Asp Pro Asn Pro Gln Glu Val Val Leu Val
                85                  90                  95
Asn Val Thr Glu Asn Phe Asn Met Trp Lys Asn Asp Met Val Glu Gln
                100                 105                 110
Met His Glu Asp Ile Ile Ser Leu Trp Asp Gln Ser Leu Lys Pro Cys
                115                 120                 125
Val Lys Leu Thr Pro Leu Cys Val Ser Leu Lys Cys Thr Asp Leu Lys
                130                 135                 140
Asn Asp Thr Asn Thr Ser Asn Asn Val Thr Ser Ser Ser Trp Gly Arg
145                 150                 155                 160
Asn Ile Met Glu Glu Gly Glu Ile Lys Asn Cys Ser Phe Asn Ile Ser
                165                 170                 175
Thr Ser Ile Arg Gly Lys Val Gln Lys Glu Tyr Ala Phe Phe Tyr Lys
                180                 185                 190
Leu Asp Ile Ile Pro Ile Asp Lys Gly Asn Asp Ser Asn Asp Thr Thr
                195                 200                 205
Ser Tyr Lys Phe Thr Leu Thr Ser Cys Asn Thr Ser Val Ile Thr Gln
                210                 215                 220
Ala Cys Pro Lys Val Ser Phe Glu Pro Ile Pro Ile His Tyr Cys Ala
225                 230                 235                 240
Pro Ala Gly Phe Ala Ile Leu Lys Cys Asn Asn Lys Thr Phe Asn Gly
                245                 250                 255
Thr Gly Pro Cys Thr Asn Val Ser Thr Val Gln Cys Thr His Gly Ile
                260                 265                 270
Arg Pro Val Val Ser Thr Gln Leu Leu Leu Asn Gly Ser Leu Ala Glu
                275                 280                 285
Glu Glu Val Val Ile Arg Ser Ala Asn Phe Thr Asp Asn Ala Lys Thr
                290                 295                 300
Ile Ile Val Gln Leu Asn Gln Ser Val Glu Ile Asn Cys Thr Arg Pro
305                 310                 315                 320
Asn Asn Asn Thr Arg Lys Ser Ile Arg Ile Gln Arg Gly Phe Gly Arg
                325                 330                 335
Ala Phe Val Thr Ile Gly Lys Ile Leu Gly Asn Met Arg Gln Ala His
                340                 345                 350
Cys Asn Ile Ser Arg Ala Lys Trp Asn Asn Thr Leu Lys Gln Ile Asp
                355                 360                 365
Ser Lys Leu Arg Glu Gln Phe Gly Asn Asn Lys Thr Ile Ile Phe Lys
                370                 375                 380
Gln Ser Ser Gly Gly Asp Pro Glu Ile Val Thr His Ser Phe Asn Cys
385                 390                 395                 400
Gly Gly Glu Phe Phe Tyr Cys Asn Ser Thr Gln Leu Phe Asn Ser Thr
                405                 410                 415
```

-continued

```
Trp Phe Asn Ser Thr Trp Ser Thr Lys Gly Ser Asn Thr Glu Gly
            420                 425                 430
Ser Asp Thr Ile Thr Leu Pro Cys Arg Ile Lys Gln Ile Ile Asn Met
            435                 440                 445
Trp Gln Glu Val Gly Lys Ala Met Tyr Ala Pro Pro Ile Ser Gly Gln
            450                 455                 460
Ile Arg Cys Ser Ser Asn Ile Thr Gly Leu Leu Leu Thr Arg Asp Gly
465                 470                 475                 480
Gly Ala Asn Glu Asn Asn Glu Ser Glu Ile Phe Arg Pro Gly Gly Gly
                    485                 490                 495
Asp Met Arg Asp Asn Trp Arg Ser Glu Leu Tyr Lys Tyr Lys Val Val
            500                 505                 510
Lys Ile Glu Pro Leu Gly Val Ala Pro Thr Lys Ala Lys Arg Arg Val
            515                 520                 525
Val Gln Arg Glu Lys Arg Ala Val Gly Glu Ile Gly Ala Leu Phe Leu
            530                 535                 540
Gly Phe Leu Gly Ala Ala Gly Ser Thr Met Gly Ala Ala Ser Met Thr
545                 550                 555                 560
Leu Thr Val Gln Ala Arg Gln Leu Leu Ser Gly Ile Val Gln Gln Gln
                    565                 570                 575
Asn Asn Leu Leu Arg Ala Ile Glu Ala Gln Gln His Leu Leu Gln Leu
            580                 585                 590
Thr Val Trp Gly Ile Lys Gln Leu Gln Ala Arg Ile Leu Ala Val Glu
            595                 600                 605
Arg Tyr Leu Lys Asp Gln Gln Leu Leu Gly Ile Trp Gly Cys Ser Gly
            610                 615                 620
Lys Leu Ile Cys Thr Thr Ala Val Pro Trp Asn Ala Ser Trp Ser Asn
625                 630                 635                 640
Lys Ser Leu Glu Gln Ile Trp Asn Asn Met Thr Trp Met Glu Trp Asp
                    645                 650                 655
Arg Glu Ile Asn Asn Tyr Thr Ser Leu Ile His Ser Leu Ile Glu Glu
            660                 665                 670
Ser Gln Asn Gln Gln Glu Lys Asn Glu Gln Glu Leu Leu Glu Leu Asp
            675                 680                 685
Lys Trp Ala Ser Leu Trp Asn Trp Phe Asn Ile Thr Asn Trp Leu Trp
            690                 695                 700
Tyr Ile Lys Leu Phe Ile Met Ile Val Gly Gly Leu Val Gly Leu Arg
705                 710                 715                 720
Ile Val Phe Ala Val Leu Ser Val Val Asn Arg Val Arg Gln Gly Tyr
                    725                 730                 735
Ser Pro Leu Ser Phe Gln Thr His Leu Pro Ile Pro Arg Gly Pro Asp
            740                 745                 750
Arg Pro Glu Gly Ile Glu Glu Gly Gly Glu Arg Asp Arg Asp Arg
            755                 760                 765
Ser Ile Arg Leu Val Asn Gly Ser Leu Ala Leu Ile Trp Asp Asp Leu
            770                 775                 780
Arg Ser Leu Cys Leu Phe Ser Tyr His Arg Leu Arg Asp Leu Leu Leu
785                 790                 795                 800
Ile Val Thr Arg Ile Val Glu Leu Leu Gly Arg Arg Gly Trp Glu Ala
                    805                 810                 815
Leu Lys Tyr Trp Trp Asn Leu Leu Gln Tyr Trp Ser Gln Glu Leu Lys
            820                 825                 830
Asn Ser Ala Val Ser Leu Leu Asn Ala Thr Ala Ile Ala Val Ala Glu
```

-continued

```
                835                 840                 845
Gly Thr Asp Arg Val Ile Glu Val Val Gln Gly Ala Tyr Arg Ala Ile
    850                 855                 860

Arg His Ile Pro Arg Ile Arg Gln Gly Leu Glu Arg Ile Leu Leu
865                 870                 875                 880
```

BI-FUNCTIONAL PLASMID THAT CAN ACT AS BOTH A DNA VACCINE AND A RECOMBINANT VIRUS VECTOR

CONTINUING INFORMATION

The present Application is a Division of application Ser. No. 08/788,815, filed Jan. 23, 1997, now U.S. Pat. No. 5,846,546, issued Dec. 8, 1998 which is a Continuation-In-Part of application Ser. No. 08/590,288, filed Jan. 23, 1996, now U.S. Pat. No. 5,741,492, issued Apr. 21, 1998, the disclosures of which are incorporated herein by reference in their entireties. Applicants claim the benefits of these Applications under 35 U.S.C. §120.

This work was supported in part by NCI grants R01-CA57419-03 and Cancer Center Support Core Grant P30-CA21765, NIH-NIAID grants AI-32529 and P01-AI31596-04. Accordingly, the U.S. Government has certain rights in this invention.

FIELD OF THE INVENTION

The present invention relates to polyenv vaccines for human immunodeficiency virus (HIV), comprising a mixture of at least 4–40 and up to 10,000 recombinant vaccinia viruses that each express a different variant of an HIV envelope protein. The vaccines are suitable for the vaccination of mammals, including humans, in order to provide unexpectedly enhanced cellular and/or humoral immune responses to HIV infection. Additionally, the invention relates to methods for making and using such recombinant vaccinia viruses and polyenv vaccines.

BACKGROUND OF THE INVENTION

The AIDS virus is likely to claim tens of millions of lives by the year 2,000, constituting a worldwide health concern of top priority [see, DeVita, et al., *AIDS, Etiology, Diagnosis, Treatment and Prevention*, 3rd edition, J. B. Lippincott Co., Philadelphia, Pa. (1992); Wong-Staal, in *Virology*, pp 1529–1543; and Hirsch, et al., in *Virology*, pp. 1545–1570]. The design of an effective HIV vaccine poses a particular challenge to immunologists, as the reverse transcriptase enzyme involved in the replication of HIV has a high error rate. This results in many mutant HIV strains having outer coat or envelope proteins with variant protein sequences. These variant envelope proteins are often recognized as different antigens by the mammalian immune system, which produces more than $10^9$ new lymphocytes per day for the sole purpose of countering foreign antigens. B and T-cells constitute, respectively, the humoral and cellular components of the immune response.

A good example of the qualitative strength of such immune responses is shown in HIV-infected patients and in SIV-infected macaques. In each case, successive rounds of infection, immunity, and establishment of variant HIVs or SIVs occur [Wrin, et al., *J. Acquir. Immune Defic. Syndr.* 7:211–219 (1994); Burns and Desrosiers, *Cur. Topics Microbiol. Immunol.* 188:185–219 (1994)]. With each cycle, the diversity of HIV antigenic determinants (and the corresponding immune responses) are increased, such that these immune responses neutralize a broad range of SIV or HIV variants, and superinfection is largely inhibited.

However, AIDS patients develop compromised immune responses that become insufficient to prevent the HIV viral infection from overcoming the patient's immune system. This may be due in part to the establishment of HIV variants whose envelope variant proteins are not recognized by the patient's immune system and thus escape destruction (*Sci. Amer.* August 1995, pp ). In such cases, even if the immune response is capable of preventing de novo infection (e.g., persistent mutation of the virus in privileged sequestered sites), the HIV infection may ultimately overcome the patient's immune response [Pantaleo et al., *Nature* 362:355–358 (1993); Embretson, et al., *Nature* 362:359–362 (1993)].

The identification of B- and T-cell antigenic determinants among HIV proteins remains incomplete. The HIV envelope protein has been characterized as having variable (V1–V5) and constant (C1–C5) regions. A peptide representative of the V3 region has been termed the principal neutralizing determinant (PND) [Javaherian et al., *Proc. Natl. Acad. Sci. (USA)* 86:6768–6772 (1989)], although other regions of the envelope protein may also be involved in eliciting an immune response. The full length envelope protein from HIV contains about 850 to 900 amino acids, with the variation in length due to hypermutation [Starcich et al., *Cell* 45:637 (1986)].

The first vaccines against HIV evaluated in clinical trials were designed to present single envelope proteins, or portions thereof, to the immune system. However, neutralizing responses towards a single or a few envelope proteins did not recognize diverse isolates of HIV and the individuals were not protected from infection [Belshe et al., *J. Am. Med. Assoc.* 272:431–431 (1994); U.S. Pat. No. 5,169,763; PCT publication WO 87/06262; Zagury et al., *Nature* 332:728–731 (1988); Kieny et al., *Int. Conf. AIDS* 5:541 (1989); Eichberg, *Int. Conf. AIDS* 7:88 (1991); Cooney et al., *Proc. Natl. Acad. Sci. USA* 90:1882–1886 (1993), Graham et al., *J. Infect. Dis.* 166:244–252 (1992); *J. Infect. Dis.* 167:533–537 (1993); Keefer et al., *AIDS Res. Hum. Retrovir.* 10 (Suppl. 2):S139–143 (1994); Gorse, *AIDS Res. Hum. Retrovir.* 10 (Suppl. 2):141–143 (1994); McElrath et al., *J. Infect. Dis.* 169:41–47 (1994); Fauci, *Science* 264:1072–1073 (May 1994)].

Accordingly, there is a long-felt and pressing need to discover vaccines and methods that elicit an immune response that is sufficient to treat or prevent HIV infections.

SUMMARY OF THE INVENTION

The present invention is intended to overcome one or more deficiencies of the related arts. In particular, the polyenv vaccine of the invention advantageously provides a more robust immune response. The strength of the present invention lies in its power to recruit B cell, helper T cell, and cytotoxic T cell compartments of the immune response for effective humoral and cellular immunity. For example, the present invention elicits a great breadth of HIV-specific antibody activities. HIV neutralization assays demonstrate that the antibodies elicited are of superior quality. Surprisingly, the invention can generate immune responses against "naive" HIV strains, i.e., HIV strains for which envelope proteins are not included in the polyenv cocktail.

To provide more effective HIV vaccines, the present invention provides polyenv vaccines comprising mixtures of at least 4 up to about 10,000, preferably 4 to about 1,000, and more preferably about 10 to about 100, different recombinant viruses, each expressing a different HIV envelope protein variant (EPV) (or a substantial portion thereof) that includes both constant and variable regions of the envelope protein. Preferably, each of the expressed envelope protein variants have a structure and/or immunogenicity similar to that of a native HIV envelope protein existing in an infected cell or HIV lipid bilayer, such as in an oligomeric form. Also provided are methods of making and using such recombinant viruses and polyenv vaccines. In their use as a vaccine, each of the variant envelope proteins preferably induces a different subset of B and/or T cells, each subset responding to different envelope proteins and, hence, to multiple HIV variants. A mixture of this number, type and/or structure of envelope proteins is a now-discovered method for eliciting a strong, durable HIV-specific immune response with broad spectrum neutralizing activity.

In a preferred embodiment, the recombinant viruses are selected from the group consisting of vaccinia, canary pox virus, adenovirus, and adeno-associated virus (AAV). In a specific example, infra, vaccinia virus is used to prepare a polyenv vaccine. In a preferred embodiment, a recombinant vaccinia virus vaccine of the invention is administered subcutaneously. A further advantage of the invention is that subcutaneous administration of vaccinia virus does not result in formation of a lesion, thus avoiding release of infectious vaccinia, which is a potential threat to an immunocompromised population.

Preferably, a recombinant virus polyenv vaccine of the invention comprises a lysate of the virus-infected growth cells, e.g., vero cells, which contains expressed envelope protein variants in addition to infectious virus. Inclusion of the lysate envelope protein variants, which abets the immune response, represents a particular distinction of the present invention, as generally virus is purified away from the growth cell lysate.

In the vaccines of the invention, the EV nucleotide may be isolated from patients infected with an HIV virus from a geographically restricted area, from patients infected with an HIV virus from different clades, or from laboratory isolates of HIV.

The present inventors have discovered that polyenv vaccines of the present invention elicit unexpectedly enhanced immune responses by the expression and/or presentation of multiple envelope protein variants, each containing both constant and variable regions, preferably having a structure that is substantially similar to that of a native HIV envelope protein. The enhanced immune responses recognize HIV strains in addition to those strains expressing the envelope proteins provided in the polyenv vaccine. Thus, the aim of such a vaccine is to provide enhanced immune responses to a wide range of HIV strains, which immune responses are suitable for treating or preventing infection (or continued infection due to mutation) by different strains of the virus.

The present invention also provides env variant (EV) nucleic acid encoding (or complementary to) at least one antigenic determinant of an envelope protein variant (EPV). The EPV is preferably encoded by a recombinant virus, as further provided in a polyenv vaccine of the present invention. The variant nucleic acid comprises at least one mutation that confers differing antigenic properties, or three dimensional structure, to the encoded EPV.

The present invention also provides a vaccine composition comprising a polyenv vaccine of the present invention, and a pharmaceutically acceptable carrier or diluent. The vaccine composition can further comprise an adjuvant and/or cytokine which enhances a polyenv vaccine immune response to at least one HIV strain in a mammal administered the vaccine composition. A polyenv vaccine of the present invention is capable of inducing an immune response inclusive of at least one of a humoral immune response (e.g., antibodies) and a cellular immune response (e.g., activation of B cells, helper T cells, and cytotoxic T cells (CTLs)).

The present invention also provides a method for eliciting an immune response to an HIV infection in a mammal which is prophylactic for an HIV infection, the method comprising administering to a mammal a vaccine composition comprising a polyenv vaccine of the present invention, which is protective for the mammal against a clinical HIV-related pathology caused by infection of at least one HIV strain.

The present invention also provides a method for eliciting an immune response to an HIV infection in a mammal for therapy of an HIV infection. The method comprises administering to a mammal a composition comprising an inactivated or attenuated polyenv vaccine of the present invention, which composition elicits an enhanced immune response, relative to controls, in the mammal against a clinical virus pathology caused by infection with at least one HIV strain.

In a further embodiment, the prophylactic or therapeutic method of eliciting an immune response to HIV comprising administering an effective amount of another (e.g., second) polyenv vaccine comprising at least 4 to about 10,000 different recombinant viruses, in which the recombinant viruses are of a different species from the recombinant viruses of the preceding vaccine, and each of the recombinant viruses in the polyenv comprises an env variant nucleotide encoding a different envelope protein variant of an HIV envelope protein.

The HIV-specific immune response generated with the polyenv recombinant virus vaccine of the invention can be further augmented by priming or boosting a humoral or cellular immune response, or both, by administering an effective amount of at least one recombinant HIV env protein, or a DNA vaccine, or both. Preferably the recombinant protein or DNA vaccine is also a polyenv vaccine. Any of the vaccine strategies provided herein can be provided in any order. For example, a subject may be primed with a recombinant virus polyenv vaccine, followed by boosting with a DNA vaccine, with a final boost with a recombinant protein vaccine. Preferably, the recombinant HIV env protein is in an admixture with an adjuvant. In a specific embodiment, exemplified infra, the recombinant HIV env protein is administered intramuscularly. Preferably, a DNA vaccine is administered with a gene gun.

The foregoing methods of the invention provide the incentive to genetically engineer a new plasmid vector. Thus, in a corollary aspect, the present invention provides a bi-functional plasmid that can serve as a DNA vaccine and a recombinant virus vector, comprising a heterologous insertion site under control of both an animal expression control sequence, and a viral expression control sequence. Preferably, the animal expression control sequence is a cytomegalovirus immediate early (CMV) promoter, and the virus expression control sequence is a vaccinia virus early promoter, a vaccinia virus late promoter, or both.

Other objects, features, advantages, utilities and embodiments of the present invention will be apparent to skilled practitioners from the following detailed description and examples relating to the present invention.

BRIEF DESCRIPTION OF THE FIGURES

FIG. 1. Schematic representation of the orientation of the HIV-1 gene in a vaccinia virus genome. The HIV-1 envelope gene is positioned between right and left segments of the thymidine kinase locus. A HindIII site exists at the C-terminus of the HIV-1 envelope gene. The appropriate insertion yields a HindIII fragment of approximately 7 kb in size. Southern blots with this pattern confirmed the position and correct orientation of the HIV-1 envelope gene.

FIG. 2. Graphical representation of data showing that the HIV-specific antibody response is long term in mammal models. The results of representative mouse sera tested in the ELISA for HIV-specific antibodies are shown. Each sample was diluted 1:100 (solid bars), 1:1,000 (hatched bars) and 1:10,000 (clear bars) prior to assay on HIV-1-coated ELISA plates. Test mice were sampled at various times (1 month, 4 months and 6 months) following the injection of $10^7$ pfu of a vaccinia virus construct expressing one envelope protein of HIV-1. The control mouse was immunized with a vaccinia virus containing no envelope sequence. Standard error bars are shown.

FIG. 3. Graphical representation of data showing how the vaccinia virus dose affects the induction of at least one immune response, including HIV-specific antibody production. Representative mouse serum samples were tested by the ELISA on HIV-1-coated plates. Serum samples were taken from mice injected with $10^5$, $10^6$, and $10^7$ pfu of one vaccinia virus expressing the HIV-1-envelope protein. Serum samples were tested approximately three weeks after injection. Each sample was diluted 1:100 (solid bars), 1:1,000 (hatched bars) and 1:10,000 (clear bars) prior to assay on HIV-1-coated ELISA plates. Standard error bars are shown.

FIG. 4. Graphical representation of data showing that the mixing of vaccinia virus constructs does not compromise the elicitation of HIV-specific antibody in injected mammals. Representative mouse serum samples were tested by the ELISA approximately 2 months following the injection of $10^7$ pfu vaccinia virus expressing HIV-1 envelope protein(s). "Single" identifies a sample from am mouse that received a single vaccinia virus. "Mix" represents a sample from a mouse that received a mixture of vaccinia viruses expressing five distinct envelope proteins. Each sample was diluted 1:100 (solid bars), 1:1,000 (hatched bars) and 1:10,000 (clear bars) prior to assay on HIV-1-coated ELISA plates. Standard error bars are shown.

FIG. 5. Production of novel vaccinia virus recombination by the substitution of PCR products for pEvenv4 BH10 sequences. The method of sequence substitution is shown. PCR products were substituted for respective BH10 env sequences at the unique enzyme restriction sites of KpnI and BsmI. Following the cutting of plasmid and ligation with PCR products, new plasmids were recombined with the wildtype VV to create VV-expression vectors.

FIG. 6. Responses in the Abbott ELISA following immunization. Sera from all four chimpanzees were tested with the Abbott clinical assay (see Materials and Methods, infra). Results for each serum sample (Y-axis) are recorded for each test date (X-axis). High responses were observed in chimps immunized with the mixed VVenv vaccine.

FIG. 7. Map of bi-functional plasmid that can act both as a DNA vaccine and as a VV recombination vector. The presence of cytomegalovirus immediate early (CMV) promoter and vaccinia virus (VV) late and early promoters permit expression of the foreign gene in both mammalian cells or VV infected cells.

DETAILED DESCRIPTION OF THE DISCLOSURE

Figure 1:
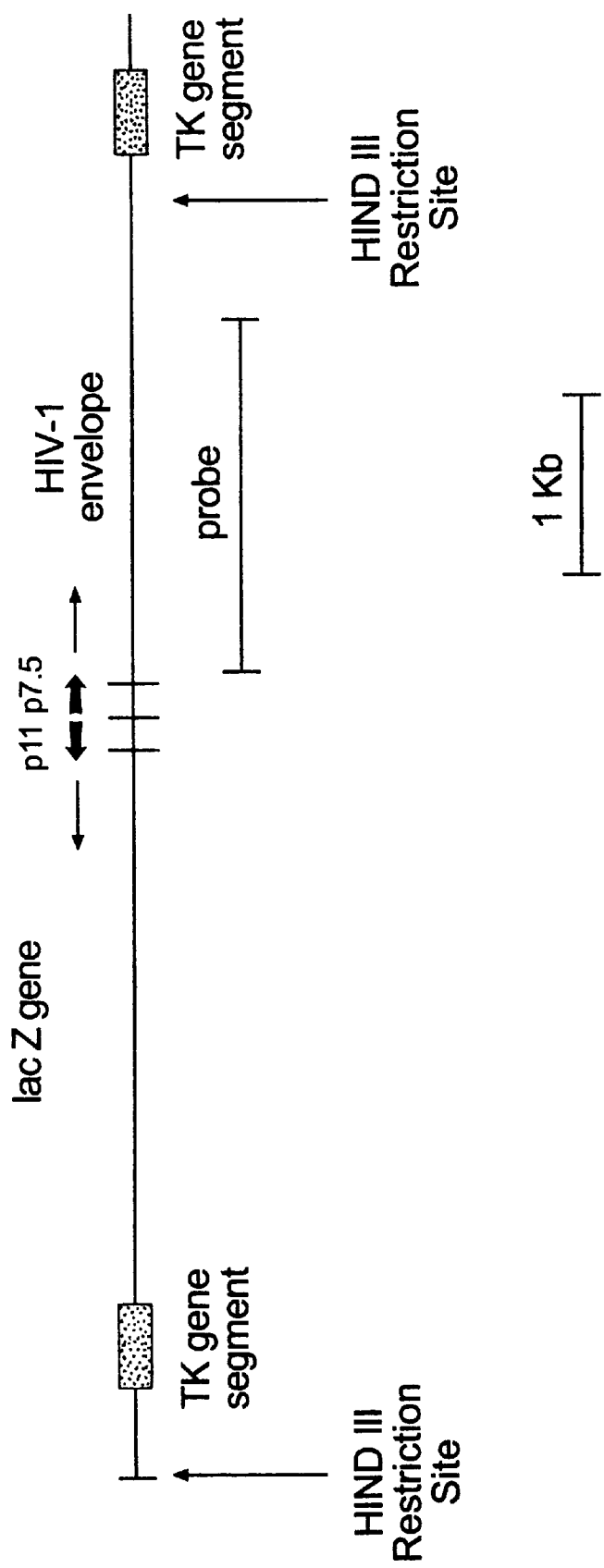
Figure 2:
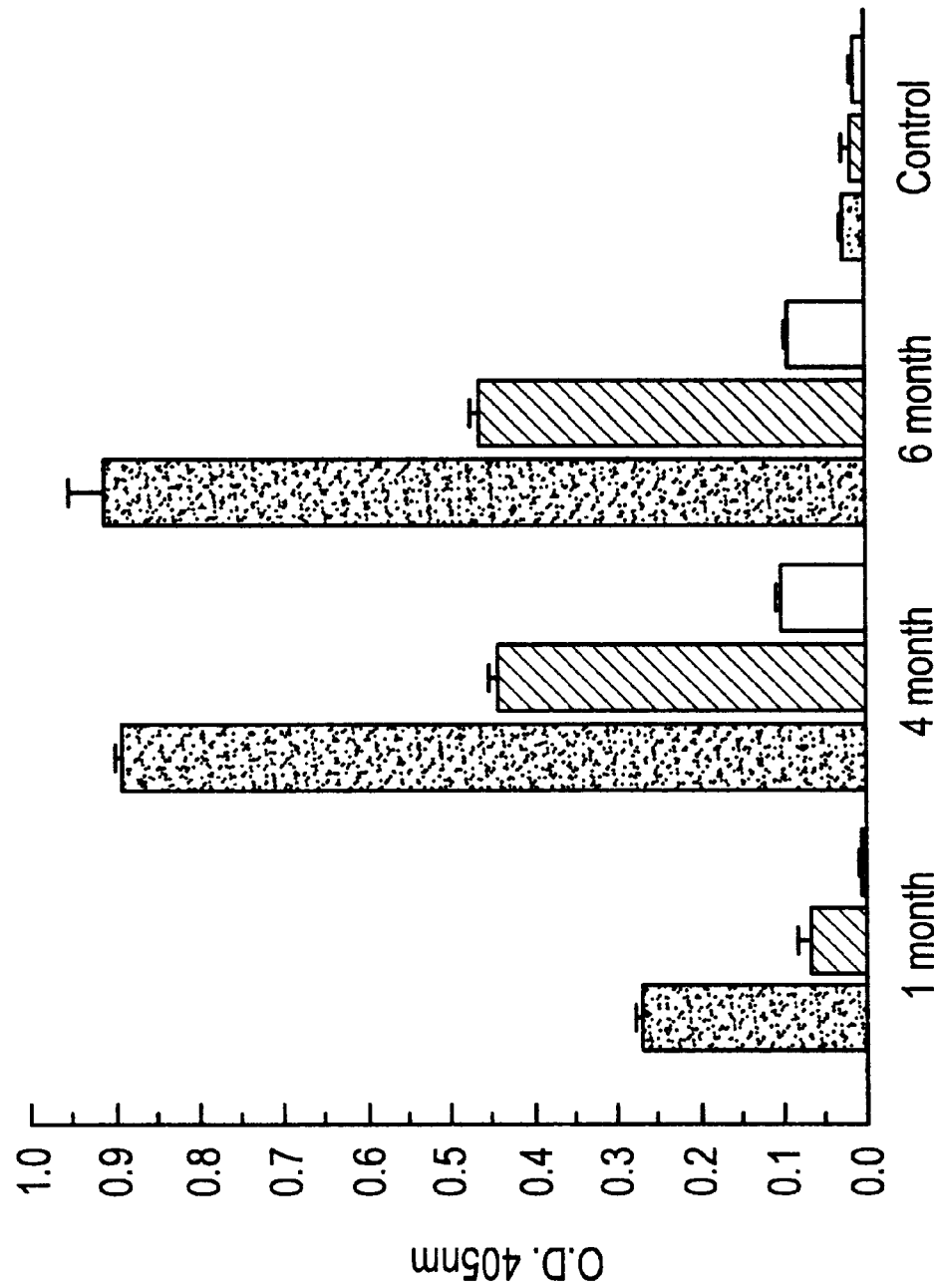
Figure 3:
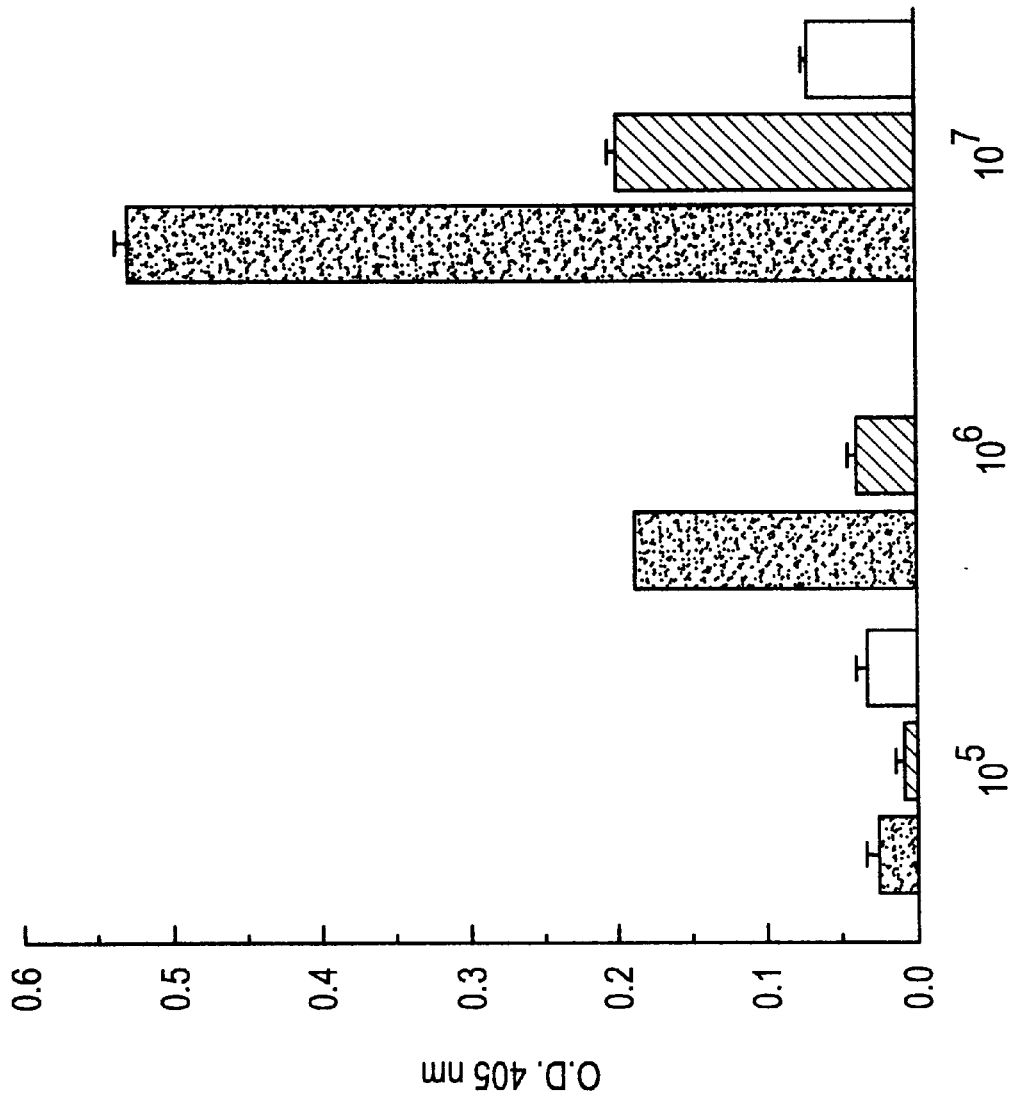
Figure 4:
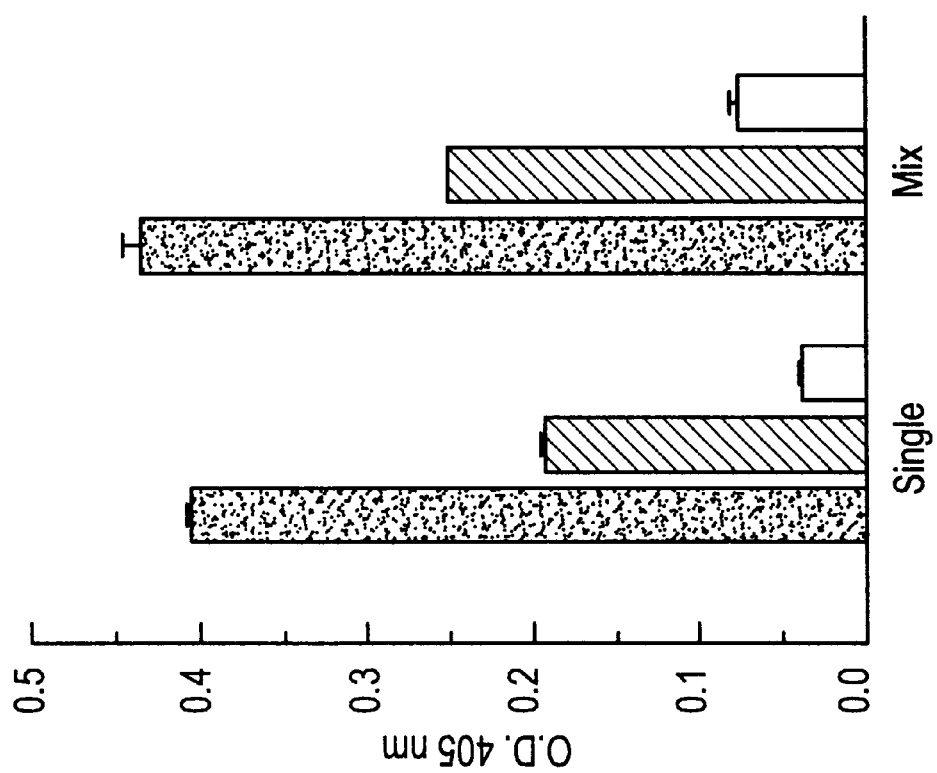
Figure 5:
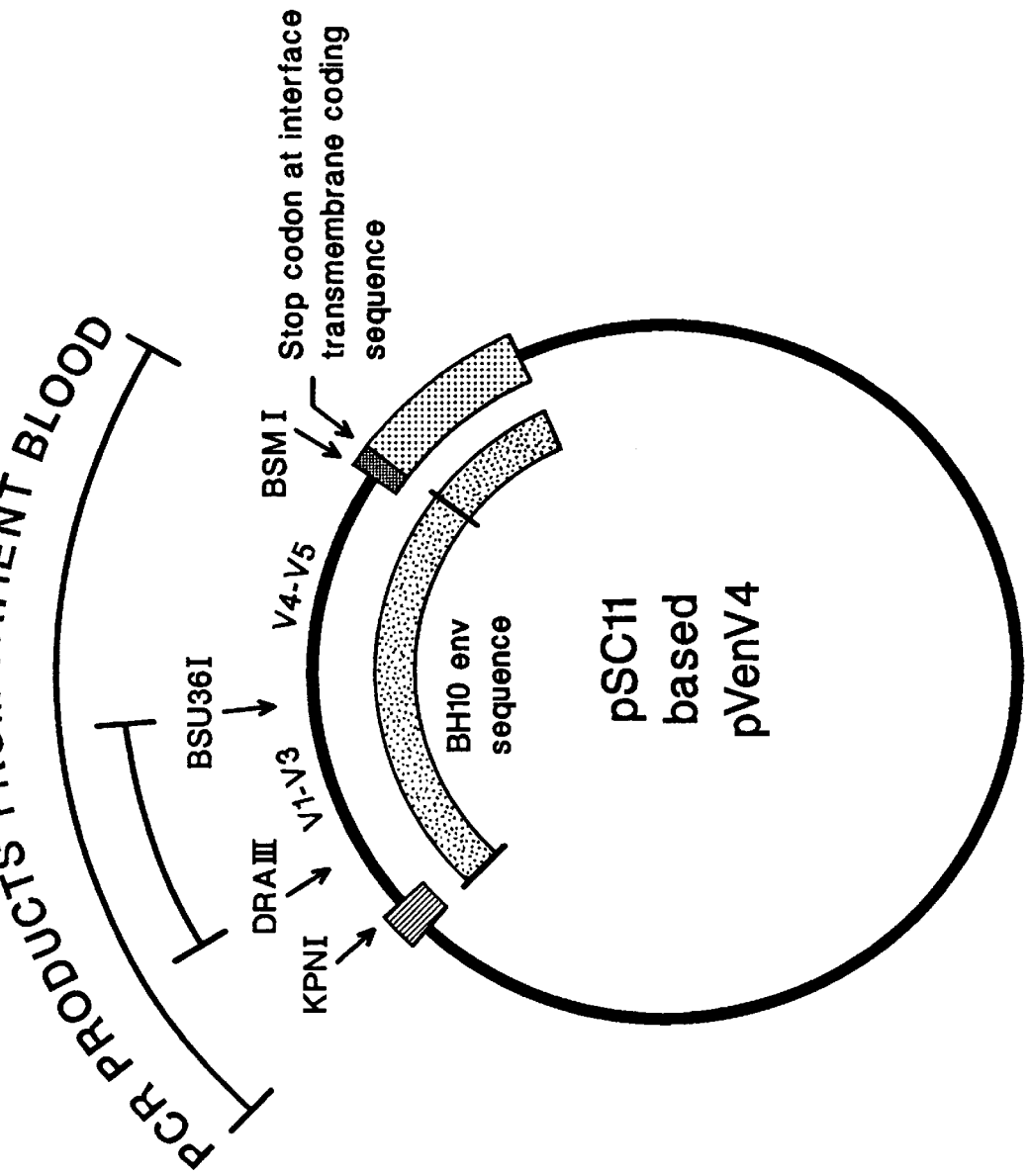
Figure 6:
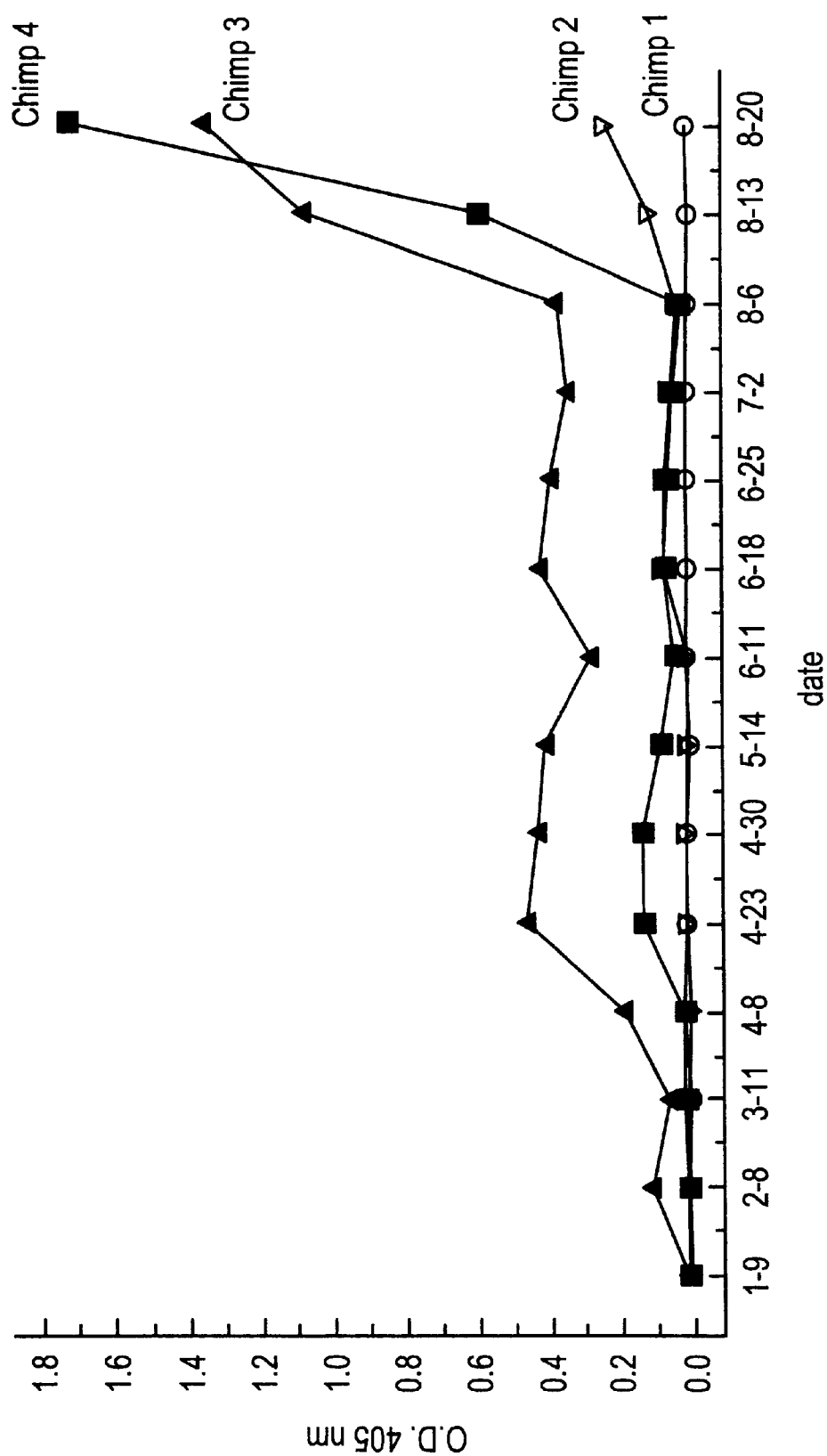

Discovery of Unexpectedly Enhanced Immune Responses to Mixed HIV Polyenv Vaccines. Previous attempts to provide vaccines against different strains of HIV have focused on one or more variable regions of gp120 or gp160. It was expected that such variable regions, provided in a vaccine, would provide broad protection against HIV infection. However, such vaccines have not been successful, where the vaccine-induced immune response does not recognize many different strains of HIV. Therefore, a critical need exists to provide vaccines that elicit immune responses to multiple strains of HIV, such that the vaccines are suitable for treatment and/or prevention of HIV.

The present inventors have discovered that unexpectedly enhanced primary and secondary (boosting) immune responses can be induced against several or many different HIV strains, by the use of polyenv vaccines that contain a mixture of at least 4, up to as many as 1,000, and possibly as many as 10,000, recombinant viruses that each encode a different envelope protein variant (EPV). The vaccine can also contain EPVs expressed by the viruses, e.g., as produced in the host cells used for virus production.

The terms "priming" or "primary" and "boost" or "boosting" are used herein to refer to the initial and subsequent immunizations, respectfully, i.e., in accordance with the definitions these terms normally have in immunology.

The EPV encoding nucleic acid (envelope variant (EV) nucleic acid) can be isolated from the same or different population (e.g., geographic) of humans infected with HIV. Alternatively, the different EV nucleic acids can be obtained from any source and selected based on screening of the sequences for differences in coding sequence or by evaluating differences in elicited humoral and/or cellular immune responses to multiple HIV strains, in vitro or in vivo, according to known methods.

The initial discovery related to recombinant vaccinia virus vaccines. However, as can be readily appreciated by one of ordinary skill in the art, any recombinant virus can be used to express polyenv antigens for a vaccine of the invention. Furthermore, the use of multiple viral vaccines can obviate anti-viral immune responses that may render a booster with the viral vaccine less effective (due to possible potentiation of a vigorous anti-virus response).

As is readily appreciated by one of skill in the art, the inventors have further found that boosting with recombinant HIV env protein or proteins, preferably proteins, further potentiates the immunization methods of the invention. The HIV env protein or proteins may correspond to the HIV env proteins expressed in the polyenv vaccine, or they may be different HIV env proteins.

Similarly, as can be appreciated by the skilled artisan, the immunization methods of the present invention are enhanced by use of a DNA vaccine. The DNA vaccine can be used as a boost, e.g., as described above with respect to the recombinant HIV proteins. Alternatively, the DNA vaccine can be used to prime immunity, with the recombinant viral vaccine or vaccines used to boost the anti-HIV immune response. As with the recombinant env protein booster vaccine, the DNA vaccine may comprise one or more vectors for expression of one or more HIV env genes. In addition, the HIV env genes may correspond to genes expressed by the recombinant virus vaccine, or they may be different. In a preferred embodiment, vectors are prepared for expression in the recombinant virus vaccine and in transfected mammalian cells as part of a DNA vaccine.

This immune response (as humoral and/or cellular) is found to be effective for a broader range of strains of an infectious virus, such as HIV, and is not limited to the virus strains expressing the specific envelope protein variants (EPVs) provided by the polyenv vaccine. The present invention thus provides multiple EPVs encoded by a recombinant viral vaccine which give unexpectedly enhanced immune responses to multiple strains of HIV.

Polyenv Vaccines and Vaccination

The present invention thus provides, in one aspect, polyenv vaccines using mixtures of at least 4, and up to 10,000 different recombinant vaccinia viruses that each express a different envelope protein variant, or an antigenic portion thereof. As can be readily appreciated to one of skill in the art, 4 to about 1000, or preferably about 10 to about 100, different recombinant viruses could be employed. One of ordinary skill in the art can further readily appreciate that other viruses can be used for vaccines. Examples of suitable viruses that can act as recombinant viral hosts for vaccines, in addition to vaccinia, includes canarypox, adenovirus, and adeno-associated virus. Also provided are methods of making and using such polyenv vaccines.

A polyenv vaccine of the present invention induces at least one of a humoral and a cellular immune response in a mammal who has been administered the polyenv vaccine, but the response to the vaccine is subclinical, or is effective in enhancing at least one immune response to at least one strain of HIV, such that the vaccine administration is suitable for vaccination purposes.

Viral vaccines. Various genetically engineered virus hosts ("recombinant viruses") can be used to prepare polyenv viral vaccines for administration of HIV polyenv antigens. Viral vaccines are particularly advantageous, in that the viral infection component promotes a vigorous immune response that targets activation of B lymphocytes, helper T lymphocytes, and cytotoxic T lymphocytes. Numerous virus species can be used as the recombinant virus hosts for the vaccines of the invention. A preferred recombinant virus for a viral vaccine is vaccinia virus [International Patent Publication WO 87/06262, Oct. 22, 1987, by Moss et al.; Cooney et al., *Proc. Natl. Acad. Sci. USA* 90:1882–6 (1993); Graham et al., *J. Infect. Dis.* 166:244–52 (1992); McElrath et al., *J. Infect. Dis.* 169:41–7 (1994)]. In another embodiment, recombinant canarypox can be used [Pialoux et al., *AIDS Res. Hum. Retroviruses* 11:373–81 (1995), erratum in *AIDS Res. Hum. Retroviruses* 11:875 (1995); Andersson et al., *J. Infect. Dis.* 174:977–85 (1996); Fries et al., *Vaccine* 14:428–34 (1996); Gonczol et al., *Vaccine* 13:1080–5 (1995)]. Another alternative is defective adenovirus or adenovirus [Gilardi-Hebenstreit et al., *J. Gen. Virol.* 71:2425–31 (1990); Prevec et al., *J. Infect. Dis.* 161:27–30 (1990); Lubeck et al., *Proc. Natl. Acad. Sci. USA* 86:6763–7 (1989); Xiang et al., *Virology* 219:220–7 (1996)]. Other suitable viral vectors include retroviruses that are packaged in cells with amphotropic host range [see Miller, *Human Gene Ther.* 1:5–14 (1990); Ausubel et al., *Current Protocols in Molecular Biology, §* 9], and attenuated or defective DNA virus, such as but not limited to herpes simplex virus (HSV) [see, e.g., Kaplitt et al., *Molec. Cell. Neurosci.* 2:320–330 (1991)], papillomavirus, Epstein Barr virus (EBV), adeno-associated virus (AAV) [see, e.g., Samulski et al., *J. Virol.* 61:3096–3101 (1987); Samulski et al., *J. Virol.* 63:3822–3828 (1989)], and the like.

DNA vaccines. An alternative to a traditional vaccine comprising an antigen and an adjuvant involves the direct in vivo introduction of DNA encoding the antigen into tissues of a subject for expression of the antigen by the cells of the subject's tissue. Such vaccines are termed herein "DNA vaccines" or "nucleic acid-based vaccines." DNA vaccines are described in International Patent Publication WO 95/20660 and International Patent Publication WO 93/19183, the disclosures of which are hereby incorporated by reference in their entireties. The ability of directly injected DNA that encodes a viral protein to elicit a protective immune response has been demonstrated in numerous experimental systems [Conry et al., *Cancer Res.,* 54:1164–1168 (1994); Cox et al., *Virol,* 67:5664–5667 (1993); Davis et al., *Hum. Mole. Genet.,* 2:1847–1851 (1993); Sedegah et al., *Proc. Natl. Acad. Sci.,* 91:9866–9870 (1994); Montgomery et al., *DNA Cell Bio.,* 12:777–783 (1993); Ulmer et al., *Science,* 259:1745–1749 (1993); Wang et al., *Proc. Natl. Acad. Sci.,* 90:4156–4160 (1993); Xiang et al., *Virology,* 199:132–140 (1994)]. Studies to assess this strategy in neutralization of influenza virus have used both envelope and internal viral proteins to induce the production of antibodies, but in particular have focused on the viral hemagglutinin protein (HA) [Fynan et al., *DNA Cell. Biol.,* 12:785–789 (1993A); Fynan et al., *Proc. Natl. Acad. Sci.,* 90:11478–11482 (1993B); Robinson et al., *Vaccine,* 11:957, (1993); Webster et al., *Vaccine,* 12:1495–1498 (1994)].

Vaccination through directly introducing DNA that encodes an HIV env protein to elicit a protective immune response produces both cell-mediated and humoral responses. This is analogous to results obtained with live viruses [Raz et al., *Proc. Natl. Acad. Sci.,* 91:9519–9523 (1994); Ulmer, 1993, supra; Wang, 1993, supra; Xiang, 1994, supra]. Studies with ferrets indicate that DNA vaccines against conserved internal viral proteins of influenza, together with surface glycoproteins, are more effective against antigenic variants of influenza virus than are either inactivated or subvirion vaccines [Donnelly et al., *Nat. Medicine,* 6:583–587 (1995)]. Indeed, reproducible immune responses to DNA encoding nucleoprotein that last essentially for the lifetime of the animal have been reported in mice [Yankauckas et al., *DNA Cell Biol.,* 12: 771–776 (1993)].

As is well known in the art, a large number of factors can influence the efficiency of expression of antigen genes and/or the immunogenicity of DNA vaccines. Examples of such factors include the reproducibility of inoculation, construction of the plasmid vector, choice of the promoter used to drive antigen gene expression and stability of the inserted gene in the plasmid. Depending on their origin, promoters differ in tissue specificity and efficiency in initiating mRNA synthesis [Xiang et al., *Virology,* 209:564–579 (1994); Chapman et al., *Nucle. Acids. Res.,* 19:3979–3986 (1991)]. To date, most DNA vaccines in mammalian systems have relied upon viral promoters derived from cytomegalovirus (CMV). These have had good efficiency in both muscle and skin inoculation in a number of mammalian species. Another factor known to affect the immune response elicited by DNA immunization is the method of DNA delivery; parenteral routes can yield low rates of gene transfer and produce considerable variability of gene expression [Montgomery, 1993, supra]. High-velocity inoculation of plasmids, using a gene-gun, enhanced the immune responses of mice [Fynan, 1993B, supra; Eisenbraun et al., *DNA Cell Biol.,* 12: 791–797 (1993)], presumably because of a greater efficiency of DNA transfection and more effective antigen presentation by dendritic cells. Vectors containing the nucleic acid-based vaccine of the invention may also be introduced into the desired host by other methods known in the art, e.g., transfection, electroporation, microinjection, transduction, cell fusion, DEAE dextran, calcium phosphate precipitation, lipofection (lysosome fusion), or a DNA vector transporter [see, e.g., Wu et al., *J. Biol. Chem.* 267:963–967 (1992); Wu and Wu, *J. Biol. Chem.* 263:14621–14624 (1988); Hartmut et al., Canadian Patent Application No. 2,012,311, filed Mar. 15, 1990].

Bi-functional plasmids for virus and DNA vaccines. A preferred aspect of the present invention concerns engineering of bi-functional plasmids that can serve as a DNA vaccine and a recombinant virus vector. Direct injection of the purified plasmid DNA, i.e., as a DNA vaccine, would elicit an immune response to the antigen expressed by the plasmid in test subjects. The plasmid would also be useful in live, recombinant viruses as immunization vehicles.

Figure 7:
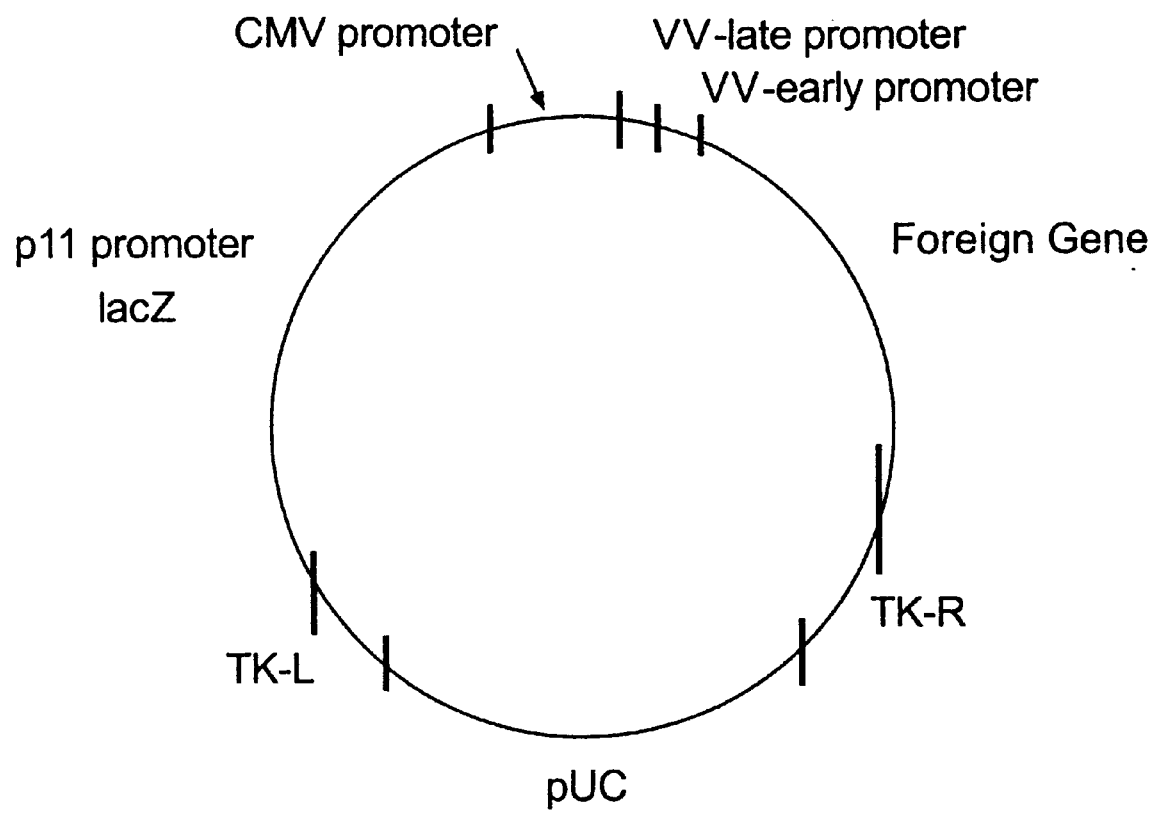

The bi-functional plasmid of the invention provides a heterologous gene, or an insertion site for a heterologous gene, under control of two different expression control sequences: an animal expression control sequence, and a viral expression control sequence. The term "under control" is used in its ordinary sense, i.e., operably or operatively associated with, in the sense that the expression control sequence, such as a promoter, provides for expression for expression of a heterologous gene. In a preferred embodiment, the animal expression control sequence is a mammalian promoter (avian promoters are also contemplated by the present invention); in a specific embodiment, the promoter is cytomegalovirus immediate early (CMV) promoter (see FIG. 7). In a further specific embodiment, the virus promoter is a vaccinia virus early promoter, or a vaccinia virus late promoter, or preferably both (FIG. 7). Subjects could be vaccinated with a multi-tiered regimen, with the bi-functional plasmid administered as DNA and, at a different time, but in any order, as a recombinant virus vaccine. The invention contemplates single or multiple administrations of the bi-functional plasmid as a DNA vaccine or as a recombinant virus vaccine, or both. This vaccination regimen may be complemented with administration of recombinant protein vaccines (infra), or may be used with additional vaccine vehicles.

As one of ordinary skill in the art can readily appreciate, the bi-functional plasmids of the invention can be used as polyenv vaccine vectors. Thus, by inserting at least 4 to about 10,000, preferably 4 to 1000, and more preferably 10 to 100, different HIV env genes into bi-functional plasmids, thus preparing a corresponding set of bi-functional plasmids useful as a polyenv vaccine.

Recombinant protein vaccines. Active immunity elicited by vaccination with an HIV env protein or proteins according to the present invention can prime or boost a cellular or humoral immune response. The HIV env protein or proteins, or antigenic fragments thereof, can be prepared in an admixture with an adjuvant to prepare a vaccine.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology, Second Ed.,* 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. Selection of an adjuvant depends on the subject to be vaccinated. Preferably, a pharmaceutically acceptable adjuvant is used. For example, a vaccine for a human should avoid oil or hydrocarbon emulsion adjuvants, including complete and incomplete Freund's adjuvant. One example of an adjuvant suitable for use with humans is alum (alumina gel). In a specific embodiment, infra, recombinant HIV env protein is administered intramuscularly in alum. Alternatively, the recombinant HIV env protein vaccine can be administered subcutaneously, intradermally, intraperitoneally, or via other acceptable vaccine administration routes.

Vaccine administration. According to the invention, immunization against HIV can be accomplished with a recombinant viral vaccine of the invention alone, or in combination with a DNA vaccine or a recombinant protein vaccine, or both. In a specific embodiment, recombinant HIV env protein in alum is provided i.m. to boost the immune response.

Each dose of virus vaccine may contain the same 4 to 10,000, preferably 4 to 1000, and more preferably 10 to 100, different recombinant viruses, each expressing a different HIV env gene. Alteratively, the viruses in subsequent vaccines may express different HIV env genes. In yet another embodiment, the subsequent polyenv viral vaccines may have some viruses in common, and others that are different, from the earlier vaccine. For example, the priming vaccine may contain vaccinia viruses expressing HIV env proteins arbitrarily designated 1–10. A second (booster) vaccine may contain vaccinia (or preferably a different virus, such as canarypox or adenovirus) viruses expressing HIV env proteins 6–15 or 11–20, etc.

A DNA vaccine or recombinant protein vaccine may have single HIV env protein antigen, or multiple antigens. Preferably, a DNA or recombinant protein vaccine for use in the invention comprises more than one HIV env protein antigen. As with subsequent viral vaccines, the HIV env protein or protein of a DNA vaccine or recombinant protein vaccine may correspond to an HIV env protein expressed in the polyenv viral vaccine, or it may be different from any of the polyenv env proteins.

In general, a preferred embodiment of the invention contemplates providing the greatest variety possible in each vaccination protocol, to expose the recipient to the largest number of HIV env proteins and thus provide the greatest opportunity for neutralizing cross-reactivity with a naive HIV isolate.

Envelope Protein Variants

As noted above, an EPV for use in the vaccines of the invention can be obtained from geographically local isolates, or clades, or from geographically diverse isolates, i.e., different clades. As can be readily appreciated by one of skill in the art, obtaining env nucleotides (i.e., genes) from natural isolates has numerous advantages: the isolates are readily available, the EVPs correspond to naturally occurring proteins to which immunity is desirable, and mutations of HIV can be captured quickly from new isolates.

An EPV also includes polypeptides having immunogenic activity elicited by an amino acid sequence of an EPV amino acid sequence as at least one epitope or antigenic determinant. This amino acid sequence substantially corresponds to at least one 10–900 amino acid fragment and/or consensus sequence of a known HIV EPV. Such an EPV can have overall homology or identity of at least 50% to a known envelope protein amino acid sequence, such as 50–99% homology, or any range or value therein, while eliciting an immunogenic response against at least one strain of an HIV.

Percent homology can be determined, for example, by comparing sequence information using the GAP computer program, version 6.0. available from the University of Wisconsin Genetics Computer Group (UWGCG). The GAP program utilizes the alignment method of Needleman and Wunsch [*J. Mol. Biol.* 48:443 (1970)], as revised by Smith and Waterman [*Adv. Appl. Math.* 2:482 (1981)]. Briefly, the GAP program defines similarity as the number of aligned symbols (i.e., nucleotides or amino acids) which are similar, divided by the total number of symbols in the shorter of the two sequences. The preferred default parameters for the GAP program include: (1) a unitary comparison matrix (containing a value of 1 for identities and 0 for non-identities) and the weighted comparison matrix of Gribskov and Burgess, *Nucl. Acids Res.* 14:6745 (1986), as described by Schwartz and Dayhoff, eds., *Atlas of Protein Sequence and Structure*, National Biomedical Research Foundation, Washington, D.C. (1979), pp. 353–358; (2) a penalty of 3.0 for each gap and an additional 0.10 penalty for each symbol in each gap; and (3) no penalty for end gaps.

In a preferred embodiment, an EPV of the present invention is a variant form of at least one HIV envelope protein. Preferably, the EPV includes gp120 and the oligomerization domain of gp41, as gp140 [Hallenberger, et al., *Virology* 193:510–514 (1993)], entirely incorporated herein by reference).

Known HIV envelope proteins contain about 750 to 900 amino acids. Examples of such sequences are readily available from commercial and institutional HIV sequence databases, such as GENBANK, or as published compilations, such as Myers et al., eds., *Human Retroviruses and AIDS, A Compilation and Analysis of Nucleic Acid and Amino Acid Sequences*, Vol. I and II, Theoretical Biology and Biophysics, Los Alamos, N.M. (1993). Substitutions or insertions of an EPV to obtain an additional EPV, encoded by a nucleic acid for use in a recombinant virus or polyenv vaccine of the present invention, can include substitutions or insertions of at least one amino acid residue (e.g., 1–25 amino acids). Alternatively, at least one amino acid (e.g., 1–25 amino acids) can be deleted from an EPV sequence. Preferably, such substitutions, insertions or deletions are identified based on sequence determination of envelope proteins obtained by nucleotide sequencing of at least one EPV encoding nucleic acid from an individual infected with HIV.

Non-limiting examples of such substitutions, insertions or deletions preferably are made by the amplification of env DNA or RNA sequences from HIV-1 infected patients, which can be determined by routine experimentation to provide modified structural and functional properties of an envelope protein or an EPV. The EPVs so obtained preferably have different antigenic properties from the original EPV. Such antigenic differences can be determined by suitable assays, e.g., by testing with a panel of monoclonal antibodies specific for HIV envelope proteins in an ELISA assay.

Any substitution, insertion or deletion can be used as long as the resulting EPV protein elicits antibodies which bind to HIV envelope proteins, but which EPV has a different pattern than antibodies elicited by a second EPV. Each of the above substitutions, insertions or deletions can also include modified or unusual amino acid, e.g., as provided in 37 C.F.R. § 1.822(p)(2), which is incorporated herein by reference.

The following Table 1 presents non-limiting examples of alternative variants of envelope proteins of HIVs, that can be encoded by a recombinant virus according to present invention.

TABLE I

HIV Envelope Protein Variants

| | 1 | 2 | 3 | 4 | 5 | 6 | 7 | 8 | 9 | 10/1 | 2 | 3 | 4 | 5 | 6 | 7 | 8 | 9 | 20/1 | 2 | 3 | 4 | 5 | 6 | 7 | 8 | 9 | 30 |
|---|---|---|---|---|---|---|---|---|---|---|---|---|---|---|---|---|---|---|---|---|---|---|---|---|---|---|---|---|
| 1 | K | E | Q | K | T | V | A | M | | R | V | K | E | S | Q | M | K | K | Q | H | L | W | R | W | G | W | R | W | G | T |
| | E | | K | | | M | | | | K | A | M | | G | T | R | R | N | C | P | N | W | L | K | I | | T | K | G | Y | I |
| | | | | | | | | | | T | | T | M | I | K | K | S | Y | N | C | R | K | G | K | | | M | L | L | M |
| | | | | | | | | | | I | | R | | M | G | G | E | W | R | R | K | | I | | | | | T | T | Y |
| | | | | | | | | | | | | | | K | E | T | | D | W | Q | S | | S | | | | | I | | |

| | 1 | 2 | 3 | 4 | 5 | 6 | 7 | 8 | 9 | 40/1 | 2 | 3 | 4 | 5 | 6 | 7 | 8 | 9 | 50/1 | 2 | 3 | 4 | 5 | 6 | 7 | 8 | 9 | 60 |
|---|---|---|---|---|---|---|---|---|---|---|---|---|---|---|---|---|---|---|---|---|---|---|---|---|---|---|---|---|
| 31 | M | L | L | G | L | M | I | C | S | | A | T | E | K | L | W | V | T | V | Y | Y | G | V | P | V | W | K | E | A | T |
| | L | I | F | W | I | I | T | 6 | L | | V | V | S | Q | | Y | A | | | | S | | i | | I | | E | D | | E |
| | A | M | A | I | M | T | P | L | | | G | A | Q | D | | | | | | | A | | | | | | H | | | V |
| | I | A | M | L | T | P | C | | | | I | E | D | N | | | | | | | | | | | | | | | | N |
| | | T | I | A | | | | | | | N | K | V | | | | | | | | | | | | | | | | | A |

| | 1 | 2 | 3 | 4 | 5 | 6 | 7 | 8 | 9 | 70/1 | 2 | 3 | 4 | 5 | 6 | 7 | 8 | 9 | 80/1 | 2 | 3 | 4 | 5 | 6 | 7 | 8 | 9 | 90 |
|---|---|---|---|---|---|---|---|---|---|---|---|---|---|---|---|---|---|---|---|---|---|---|---|---|---|---|---|---|
| 61 | T | T | L | F | C | A | S | D | A | K | A | Y | D | T | E | V | H | N | V | W | A | T | H | A | C | V | P | T | D | P |
| | P | V | | | | | | E | R | R | T | H | S | R | | A | | K | I | C | | S | Y | | | | | | N | |
| | | | | | | | | | | N | S | T | K | A | | R | | | | | K | Q | | | | | | | G | |
| | | | | | | | | | | | L | | A | K | | Q | | | | | | | | | | | | | | |
| | | | | | | | | | | | | | E | P | | K | | | | | | | | | | | | | | |

| | 1 | 2 | 3 | 4 | 5 | 6 | 7 | 8 | 9 | 100/1 | 2 | 3 | 4 | 5 | 6 | 7 | 8 | 9 | 110/1 | 2 | 3 | 4 | 5 | 6 | 7 | 8 | 9 | 120 |
|---|---|---|---|---|---|---|---|---|---|---|---|---|---|---|---|---|---|---|---|---|---|---|---|---|---|---|---|---|
| 91 | N | P | Q | E | V | V | L | V | N | V | T | E | N | F | N | M | W | K | N | D | M | V | E | Q | M | H | E | D | I | I |
| | D | | H | | I | L | M | G | S | | | G | E | | D | I | | R | | N | I | | D | | | Q | T | | | V |
| | S | | R | | L | Y | | E | | | | D | K | | | | | T | | S | | | N | | | | | | | |
| | T | | Y | | M | D | | P | | | | | D | | | | | | | Y | | | | | | | | | | |
| | | | | | F | S | | | | | | | H | | | | | | | | | | | | | | | | | |

130  140  150

TABLE I-continued

HIV Envelope Protein Variants

|  | 1 | 2 | 3 | 4 | 5 | 6 | 7 | 8 | 9 | 1 | 2 | 3 | 4 | 5 | 6 | 7 | 8 | 9 | 1 | 2 | 3 | 4 | 5 | 6 | 7 | 8 | 9 |
|---|---|---|---|---|---|---|---|---|---|---|---|---|---|---|---|---|---|---|---|---|---|---|---|---|---|---|---|
| 121 | S | L | W | D | Q | S | L | K | P | C | V | K | L | T | P | L | C | V | S | L | K | C | T | D | L | K | N | D | T | S | N |
|  | N |  |  | E | E |  |  |  |  |  | E | V | M |  | L | C |  |  | T | M | N |  | K | H | V | T | T | A | S | E |
|  |  |  |  |  |  |  |  |  |  |  |  | N |  |  |  |  |  |  | N |  | D |  | I | N | Y | G |  | G | M | T |
|  |  |  |  |  |  |  |  |  |  |  |  | Q |  |  |  |  |  |  | Q |  | S |  | H | Q | W | R |  |  |  | I |
|  |  |  |  |  |  |  |  |  |  |  |  |  |  |  |  |  |  |  |  |  | I |  | G | K | F | L |  |  |  | S |

|  |  |  |  |  |  |  |  | 160 |  |  |  |  |  |  |  |  |  | 170 |  |  |  |  |  |  |  | 180 |
|---|---|---|---|---|---|---|---|---|---|---|---|---|---|---|---|---|---|---|---|---|---|---|---|---|---|---|
|  | 1 | 2 | 3 | 4 | 5 | 6 | 7 | 8 | 9 | 1 | 2 | 3 | 4 | 5 | 6 | 7 | 8 | 9 | 1 | 2 | 3 | 4 | 5 | 6 | 7 | 8 | 9 |
| 151 | T | S | N | N | V | T | S | S | S | W | G | R | N | I | M | E | E | G | E | I | K | N | C | S | F | N | I | S | T | S |
|  | N | K | E | S |  |  | T | T | N | N | W | K | E |  | I | D | R | R | A | K |  |  | P | Y | K | Y | Q |  | K | G |
|  | I | E |  | K |  |  | N | V |  | I | S | K |  |  | T | G | Q | A | G | M |  |  | T |  | V |  |  |  | P | N |
|  |  |  |  |  |  |  |  | G |  | S | Q | W |  |  | I |  | G | S | R | V |  |  | E |  | Q | M |  |  |  | I |
|  |  |  |  |  |  |  |  |  |  | L |  | G |  |  | V |  | N | K | L | R |  |  |  |  |  | T |  |  |  | E |
|  |  |  |  |  |  |  |  |  |  |  |  | T |  |  |  |  |  |  |  | Q |  |  |  |  |  |  |  |  |  |  |

|  |  |  |  |  |  |  |  | 190 |  |  |  |  |  |  |  |  |  | 200 |  |  |  |  |  |  |  | 210 |
|---|---|---|---|---|---|---|---|---|---|---|---|---|---|---|---|---|---|---|---|---|---|---|---|---|---|---|
|  | 1 | 2 | 3 | 4 | 5 | 6 | 7 | 8 | 9 | 1 | 2 | 3 | 4 | 5 | 6 | 7 | 8 | 9 | 1 | 2 | 3 | 4 | 5 | 6 | 7 | 8 | 9 |
| 181 | I | R | G | K | V | Q | K | E | Y | A | F | F | Y | K | L | D | I | I | P | I | D | K | G | N | D | S |  | N | D |
|  | L | G | D | R | I | K | Q | D | N | S | L | L | R | N | H |  | V | V | Q | V | K | D | S | D | I | N | P | K | D | A |
|  | V | K | & | Q | M | H | R | V | R | L | Y |  | H | R | T |  | L | A | K | V | G | N | S |  |  |  |  | T | S |
|  | R | S |  | E | K | E | T | A | S | T | T |  | N | T | P |  |  | M | E | L |  | E | G |  |  |  |  | S |  |
|  | K | T |  |  | Q |  |  | G | H |  | H |  |  | V | S |  |  | S | N |  |  | N |  |  |  |  |  |  |  |  |
|  |  |  |  |  |  |  |  |  | H |  |  |  |  |  |  |  |  |  |  |  |  |  |  |  |  |  |  |  |  |  |

|  |  |  |  |  |  |  |  | 220 |  |  |  |  |  |  |  |  |  | 230 |  |  |  |  |  |  |  | 240 |
|---|---|---|---|---|---|---|---|---|---|---|---|---|---|---|---|---|---|---|---|---|---|---|---|---|---|---|
|  | 1 | 2 | 3 | 4 | 5 | 6 | 7 | 8 | 9 | 1 | 2 | 3 | 4 | 5 | 6 | 7 | 8 | 9 | 1 | 2 | 3 | 4 | 5 | 6 | 7 | 8 | 9 |
| 211 | T |  | T | T | T | S | Y | K |  | F | T | L | T | S | C | N | T | S | V | I | T | Q | A | C | P | K | V | S | F | E |
|  | S |  | S | N | A | N |  | W |  | K | R | I | I | H |  | S | R | T | T | V | K |  |  | S |  |  | I | T |  | Q |
|  | S |  | N | I |  |  |  | N |  | Y | I |  | N |  |  | D | S |  | A | L |  |  |  |  |  |  |  | T |  | D |
|  |  |  |  |  |  |  |  | R |  |  | K |  | T |  |  |  |  |  | I |  |  |  |  |  |  |  |  |  |  |  |
|  |  |  |  |  |  |  |  | G |  |  | M |  |  |  |  |  |  |  |  |  |  |  |  |  |  |  |  |  |  |  |

|  |  |  |  |  |  |  |  | 250 |  |  |  |  |  |  |  |  |  | 260 |  |  |  |  |  |  |  | 270 |
|---|---|---|---|---|---|---|---|---|---|---|---|---|---|---|---|---|---|---|---|---|---|---|---|---|---|---|
|  | 1 | 2 | 3 | 4 | 5 | 6 | 7 | 8 | 9 | 1 | 2 | 3 | 4 | 5 | 6 | 7 | 8 | 9 | 1 | 2 | 3 | 4 | 5 | 6 | 7 | 8 | 9 |
| 241 | P | I | P | I | H | Y | C | A | P | A | G | F | A | I | L | K | C | N | N | K | T | F | N | G | T | G | P | C | T | N |
|  |  | F |  | M |  | F |  | T |  | G | T |  | Y | V | M |  | F |  | K | D |  |  | S | E |  | K | Q |  | K |  |
|  |  |  |  |  |  | H |  |  |  |  |  |  |  |  | L |  |  |  | R | S |  |  | E |  |  | S | S |  | H |  |
|  |  |  |  |  |  |  |  |  |  |  |  |  |  |  |  |  |  |  |  | P | E |  |  |  |  |  | T |  | S |  |
|  |  |  |  |  |  |  |  |  |  |  |  |  |  |  |  |  |  |  |  | T | C |  |  |  |  |  | I |  | R |  |
|  |  |  |  |  |  |  |  |  |  |  |  |  |  |  |  |  |  |  |  |   | Q |  |  |  |  |  |   |  |   |  |

|  |  |  |  |  |  |  |  | 280 |  |  |  |  |  |  |  |  |  | 290 |  |  |  |  |  |  |  | 300 |
|---|---|---|---|---|---|---|---|---|---|---|---|---|---|---|---|---|---|---|---|---|---|---|---|---|---|---|
|  | 1 | 2 | 3 | 4 | 5 | 6 | 7 | 8 | 9 | 1 | 2 | 3 | 4 | 5 | 6 | 7 | 8 | 9 | 1 | 2 | 3 | 4 | 5 | 6 | 7 | 8 | 9 |
| 271 | V | S | T | V | Q | C | T | H | G | I | R | P | V | V | S | T | Q | L | L | L | N | G | S | L | A | E | E | V | V |
|  | I | T | T | S | R |  |  |  |  |  | K |  | I |  | T |  | H |  |  | I |  | T |  | S | K | G | I | K |
|  |  |  | S | V | T |  |  |  |  |  | S |  | T |  |  |  |  |  |  | S |  |  |  |  | R | K | R | R |
|  |  |  | V |  | H |  |  |  |  |  |  |  |  |  |  |  |  |  |  |  |  |  |  |  | R | R | D | I |
|  |  |  |  |  |  |  |  |  |  |  |  |  |  |  |  |  |  |  |  |  |  |  |  |  |   | K | G |   |
|  |  |  |  |  |  |  |  |  |  |  |  |  |  |  |  |  |  |  |  |  |  |  |  |  |   | D |   | M |

|  |  |  |  |  |  |  |  | 310 |  |  |  |  |  |  |  |  |  | 320 |  |  |  |  |  |  |  | 330 |
|---|---|---|---|---|---|---|---|---|---|---|---|---|---|---|---|---|---|---|---|---|---|---|---|---|---|---|
|  | 1 | 2 | 3 | 4 | 5 | 6 | 7 | 8 | 9 | 1 | 2 | 3 | 4 | 5 | 6 | 7 | 8 | 9 | 1 | 2 | 3 | 4 | 5 | 6 | 7 | 8 | 9 |
| 301 | I | R | S | A | N | F | T | D | N | A | K | T | I | I | V | Q | L | N | Q | S | V | E | I | N | C | T | R | P | N | N |
|  | L | M | G | D | D | I | S | N | S | V | R | W | L | A |  | H |  | K | E | P | I | A | V | V | Y | I |  | E | S | I |
|  | V |  | A | E |  | L | P | E | G | T | D | N | V |  |  | T |  | T | A | T | L | Q | T | M |  | A |  |  | A | K |
|  | M |  | V | S |  | P | K | A | H |  | N | V |  |  |  |  |  |  | D | A |  | V |  |  |  | E |  |  | E | Y |
|  |  |  | S | K |  |  |  | L |  |  |  |  |  |  |  |  |  |  | T |  |  | T |  |  |  | H |  |  | H | Q |

|  |  |  |  |  |  |  |  | 340 |  |  |  |  |  |  |  |  |  | 350 |  |  |  |  |  |  |  | 360 |
|---|---|---|---|---|---|---|---|---|---|---|---|---|---|---|---|---|---|---|---|---|---|---|---|---|---|---|
|  | 1 | 2 | 3 | 4 | 5 | 6 | 7 | 8 | 9 | 1 | 2 | 3 | 4 | 5 | 6 | 7 | 8 | 9 | 1 | 2 | 3 | 4 | 5 | 6 | 7 | 8 | 9 |
| 331 | N | T | R | K | S | I | R |  | I | Q | R | G | F | G | R | A | F | V | T | T | G | K | I | L | G | N | M | R | Q | A |
|  | K | V | N | R | R |  | Y | H | R | H | I | A | P | R | K | V | I | H | A | R | R | K | S | D | I | G | K |
|  | Y | K | K | G | N |  | Y | K | M | P | S |  | S | K | T | W | H | A | T | K | Q | S | A | N |  | I |  | L |
|  | T | R | S | Q | T |  | H | M | P | S |  |  | L | M | M | S | V | T | R | L | D | V | F | T |  |  | R |
|  | S | I | P | I | G |  | P |  | L | Y |  |  |  |  | S | W | Y | I | N | M | E | A | N | I |  |  | V |
|  |  |  | V |  |  |  |  |  |  |  |  |  |  |  |  | Y |  |  |  |  |  | V |  | T |  |  |  |  |

|  |  |  |  |  |  |  |  | 370 |  |  |  |  |  |  |  |  |  | 380 |  |  |  |  |  |  |  | 390 |
|---|---|---|---|---|---|---|---|---|---|---|---|---|---|---|---|---|---|---|---|---|---|---|---|---|---|---|
|  | 1 | 2 | 3 | 4 | 5 | 6 | 7 | 8 | 9 | 1 | 2 | 3 | 4 | 5 | 6 | 7 | 8 | 9 | 1 | 2 | 3 | 4 | 5 | 6 | 7 | 8 | 9 |
| 361 | H | C | N | I | S | R | A | K | W | N | N | T | L | K | Q | I | D | S | K | L | R | E | Q | F | G | N | N | K | T | I |
|  | Y |  | K | L | A | G | E | Q |  |  | K | A | V | I | E | V | V | K | S | Y | K | K | Y | K | D |  |  | Q | S | V |
|  |  |  | T | V | N | K | T | D |  |  | S | K | A | V | Q | L | A | T | Q | Q | A | H | L | D |  |  | H |  | T |

TABLE I-continued

HIV Envelope Protein Variants

| | 1 | 2 | 3 | 4 | 5 | 6 | 7 | 8 | 9 | | 1 | 2 | 3 | 4 | 5 | 6 | 7 | 8 | 9 | | 1 | 2 | 3 | 4 | 5 | 6 | 7 | 8 | 9 | |
|---|---|---|---|---|---|---|---|---|---|---|---|---|---|---|---|---|---|---|---|---|---|---|---|---|---|---|---|---|---|---|
| | | | | Y | | E<br>A | R<br>S | N<br>A | | | E<br>F | R<br>D | | I | | S<br>N | R<br>L | T | | | E<br>R | H<br>I | | G<br>I | V<br>D | R | S | | | M |
| | | | | | | | | | | 400 | | | | | | | | | | 410 | | | | | | | | | | 420 |
| 391 | I<br>V<br>N<br>A<br>K | F<br>S<br>L | K<br>N<br>T<br>A<br>K | Q<br>H<br>S<br>K<br>N | S<br>H<br>P<br>G<br>T | S<br>A | G<br>C | G<br>C | D | P<br>L<br>I<br>V<br>Q | E | I<br>V | V<br>T<br>S | T<br>M<br>L<br>H | H<br>Y<br>L | S<br>N<br>T<br>M<br>H | F<br>L | N<br>I<br>T | C<br>V | G<br>R<br>V<br>W<br>E | G | E<br>D | F<br>I | F | Y | C | N<br>D | S<br>T<br>A | T<br>S<br>A<br>R | Q<br>G<br>N<br>P<br>K |
| | | | | | | | | | | 430 | | | | | | | | | | 440 | | | | | | | | | | 450 |
| 421 | L<br>M<br>I | F<br>D | N<br>S<br>D<br>T | S<br>N<br>T<br>G<br>A | T<br>I | W<br>Y<br>C<br>F | F<br>R<br>N<br>8<br>G | N<br>L | S<br>N<br>V<br>D | T<br>K<br>G<br>D<br>S | W<br>A<br>D<br>K<br>M | S<br>G<br>I<br>K<br>K | T<br>K<br>P<br>N<br>G | K<br>E<br>I<br>C<br>T | G<br>W<br>K<br>G<br>M | S<br>N<br>D<br>G<br>L | N<br>D<br>S<br>T<br>D | N<br>G<br>G<br>S<br>I | T<br>M<br>D<br>N<br>Q | E<br>K<br>G<br>Q | G<br>E<br>N<br>A<br>S | S<br>R<br>E<br>R<br>K | D<br>A<br>G<br>K<br>R | T<br>N<br>P<br>E<br>S | I<br>L<br>I<br>R | T<br>L<br>V<br>V<br>K | L<br>H<br>I | P<br>Q<br>L<br>D | C | R<br>K |
| | | | | | | | | | | 460 | | | | | | | | | | 470 | | | | | | | | | | 480 |
| 451 | I | K<br>E | Q<br>F | I<br>V | I | N<br>R<br>K | M<br>I<br>R<br>S<br>L | W | Q<br>A | E<br>G<br>R<br>K<br>V | V<br>T<br>A | G<br>R | K<br>Q<br>R | A<br>S<br>T<br>L<br>I | M | Y<br>D | A | P<br>L | P | I<br>F<br>T | S<br>G<br>R | G | Q<br>V<br>Q<br>K<br>E | I<br>L | R<br>S<br>T<br>L | C<br>K<br>T | S<br>F | S<br>I<br>E<br>V<br>T | N | I |
| | | | | | | | | | | 490 | | | | | | | | | | 500 | | | | | | | | | | 510 |
| 481 | T | G | L<br>T<br>I | L<br>I | L | T<br>V<br>E | R<br>S | D | G<br>S | G<br>V | A<br>T<br>E<br>D<br>G | N<br>D<br>S<br>G<br>E | E<br>Q<br>K<br>T<br>D | N<br>T<br>S<br>A<br>K | N<br>S<br>A<br>K | E<br>D<br>G<br>R<br>T | S<br>T<br>E<br>N<br>I | E<br>V<br>N<br>L | I<br>V<br>T | F<br>I<br>S<br>L | R<br>P | P<br>L | G<br>T<br>A<br>V<br>I | G | G | D<br>N<br>E | M<br>I | R<br>K | D<br>N | N<br>I |
| | | | | | | | | | | 520 | | | | | | | | | | 530 | | | | | | | | | | 540 |
| 511 | W<br>R | R<br>I | S<br>N<br>T | E | L | Y<br>K | K<br>F | Y<br>N | K | V<br>D | V<br>I | K<br>R<br>T<br>Q<br>E | I<br>V | E<br>K | P<br>L<br>T<br>F | L<br>I<br>S | G<br>V<br>I | V | A<br>P | P<br>T<br>S<br>R | K<br>A<br>S<br>P<br>M<br>I | R<br>K<br>R<br>S<br>A | R<br>P<br>H | R<br>I | V<br>M<br>I | V | Q<br>E<br>A<br>W<br>H | R |
| | | | | | | | | | | 550 | | | | | | | | | | 560 | | | | | | | | | | 570 |
| 541 | E<br>K<br>Q | K<br>E | R | A | V | G<br>I<br>A | E<br>F<br>I<br>V | I<br>T<br>A<br>L | G<br>V<br>L*<br>M | A<br>V<br>M | L<br>M<br>V<br>F<br>I | F<br>S<br>L<br>I | L<br>I<br>P | G | F<br>V | L | G<br>S | A | A<br>G<br>S | G | S | T | M<br>A | G | A<br>V<br>R<br>G<br>T | A<br>A<br>P<br>I<br>V | S<br>M<br>L<br>I<br>T | M<br>L<br>A | T<br>V<br>T | L<br>V |
| | | | | | | | | | | 580 | | | | | | | | | | 590 | | | | | | | | | | 600 |
| 571 | T<br>A | V<br>G | Q<br>R<br>P | A<br>T<br>P<br>L | R<br>H | Q<br>H<br>L<br>K<br>S | L<br>V | L<br>M<br>K | S<br>G<br>D | G | I | V<br>Q<br>H | Q | Q | N<br>S<br>D | N | L<br>L | R<br>M<br>R | A<br>I | I<br>E<br>K<br>D<br>Q | E<br>A<br>G | A<br>Q<br>Q<br>Q | Q | H<br>M | L | L | Q<br>K<br>E<br>R |
| | | | | | | | | | | 610 | | | | | | | | | | 620 | | | | | | | | | | 630 |
| 601 | L | T<br>S | V<br>I | W | G | I<br>V | K<br>R | Q | L | Q<br>R | A<br>L<br>T | R | I<br>V<br>L | L<br>Q | A<br>V<br>L<br>I | V | E<br>R<br>T<br>S | R<br>Y<br>F<br>L | Y<br>L<br>I | L<br>K<br>R<br>Q<br>G | K<br>D<br>E<br>N | D<br>Q | Q | L<br>R<br>K | L<br>R<br>I | G<br>M<br>E<br>R<br>S<br>N | I<br>F<br>M<br>N<br>L | W<br>L | G<br>W |
| | | | | | | | | | | 640 | | | | | | | | | | 650 | | | | | | | | | | 660 |
| | 1 | 2 | 3 | 4 | 5 | 6 | 7 | 8 | 9 | | 1 | 2 | 3 | 4 | 5 | 6 | 7 | 8 | 9 | | 1 | 2 | 3 | 4 | 5 | 6 | 7 | 8 | 9 | |

TABLE I-continued

HIV Envelope Protein Variants

| | 1 | 2 | 3 | 4 | 5 | 6 | 7 | 8 | 9 | 670 1 | 2 | 3 | 4 | 5 | 6 | 7 | 8 | 9 | 680 1 | 2 | 3 | 4 | 5 | 6 | 7 | 8 | 9 | 690 |
|---|---|---|---|---|---|---|---|---|---|---|---|---|---|---|---|---|---|---|---|---|---|---|---|---|---|---|---|---|
| 631 | C R | S K | G | K R | L T H I A | I V | C | T P Y | T P Y | A T N F S | V | P K | W | N | A S F N | S T A | W | S G S | N R | K R Y | S T N G | L M Q V R | E D N S K | Q D M S K | I F | W | N D G Q W | N K H T | M T L N | T M |

| | 1 | 2 | 3 | 4 | 5 | 6 | 7 | 8 | 9 | 700 1 | 2 | 3 | 4 | 5 | 6 | 7 | 8 | 9 | 710 1 | 2 | 3 | 4 | 5 | 6 | 7 | 8 | 9 | 720 |
|---|---|---|---|---|---|---|---|---|---|---|---|---|---|---|---|---|---|---|---|---|---|---|---|---|---|---|---|---|
| 661 | W | M L I Q | E Q K | W | D E | R K Q | E L H Q | I V | N D E S | N S K | Y V I | T S | S N G D K | L T I V E | I | H Y F | S T N | L I L E | I E T Q | E D D Q | S A | Q A | N I T D V | Q | Q | E G D | K I Q R | N | E Q V |

| | 1 | 2 | 3 | 4 | 5 | 6 | 7 | 8 | 9 | 730 1 | 2 | 3 | 4 | 5 | 6 | 7 | 8 | 9 | 740 1 | 2 | 3 | 4 | 5 | 6 | 7 | 8 | 9 | 750 |
|---|---|---|---|---|---|---|---|---|---|---|---|---|---|---|---|---|---|---|---|---|---|---|---|---|---|---|---|---|
| 691 | Q L R K | E D A K | L | L | E G A K Q | L | D N | K E S Q | W | A T K | S N G | L | W | N S | W | F S Y L | N S G D | I | T | N S Q K | W | L | W Y S | I | K R I | L I A | F M V | I V I | M I |

| | 1 | 2 | 3 | 4 | 5 | 6 | 7 | 8 | 9 | 760 1 | 2 | 3 | 4 | 5 | 6 | 7 | 8 | 9 | 770 1 | 2 | 3 | 4 | 5 | 6 | 7 | 8 | 9 | 780 |
|---|---|---|---|---|---|---|---|---|---|---|---|---|---|---|---|---|---|---|---|---|---|---|---|---|---|---|---|---|
| 721 | I V A | V I | G A | G A | L I I | V | G I | L V K | R | I V | V I M S T I | F | A V I F | V | L | S C N | V I L | V N K R | N R S N I | R F | Q S A | G | Y Q | S | P | L | S | F L |

| | 1 | 2 | 3 | 4 | 5 | 6 | 7 | 8 | 9 | 790 1 | 2 | 3 | 4 | 5 | 6 | 7 | 8 | 9 | 800 1 | 2 | 3 | 4 | 5 | 6 | 7 | 8 | 9 | 810 |
|---|---|---|---|---|---|---|---|---|---|---|---|---|---|---|---|---|---|---|---|---|---|---|---|---|---|---|---|---|
| 751 | Q | T I | H R L P | L H V T A P F | P Q N T I | I P T T A G | P G T R S | R E G Q | G E | P L A | D G E T | R Q T | P L D Q G E | E G | G | I R E | E T | E D | E G | G G | E D | R Q G E | D G K | R G P S K | S T W | I V G N S | R G Q P A |

| | 1 | 2 | 3 | 4 | 5 | 6 | 7 | 8 | 9 | 820 1 | 2 | 3 | 4 | 5 | 6 | 7 | 8 | 9 | 830 1 | 2 | 3 | 4 | 5 | 6 | 7 | 8 | 9 | 840 |
|---|---|---|---|---|---|---|---|---|---|---|---|---|---|---|---|---|---|---|---|---|---|---|---|---|---|---|---|---|
| 781 | L A S | V L P | N D H T S | G | S F L C | L S | A T | L I Q P Q | I F L | W Y | D E V G T | D | L C | R W G N A | S T I | L C F I G | L F S I W | S S C L T | Y | H R Q | R L S | L | R T S S | D N S C | L F A I | L S C | I T V Q H |

| | 1 | 2 | 3 | 4 | 5 | 6 | 7 | 8 | 9 | 850 1 | 2 | 3 | 4 | 5 | 6 | 7 | 8 | 9 | 860 1 | 2 | 3 | 4 | 5 | 6 | 7 | 8 | 9 | 870 |
|---|---|---|---|---|---|---|---|---|---|---|---|---|---|---|---|---|---|---|---|---|---|---|---|---|---|---|---|---|
| 811 | V A I | T A V K M | R | I T A L V | V I D S K Y | E L I T | L | L | G K R | R H L | G L L I | W | E D N | A G I V R | L I C | K R | Y W L I | W L G C A G | N S V A C | L V M T | Q L I | Y | W | S I G T L | Q K R | E | L |

| | 1 | 2 | 3 | 4 | 5 | 6 | 7 | 8 | 9 | 880 1 | 2 | 3 | 4 | 5 | 6 | 7 | 8 | 9 | 889 1 | 2 | 3 | 4 | 5 | 6 | 7 | 8 | 9 | |
|---|---|---|---|---|---|---|---|---|---|---|---|---|---|---|---|---|---|---|---|---|---|---|---|---|---|---|---|---|
| 841 | K R Q | N I S | S | A V V F | V I S T | S L N W F | L F V A | N T D A | A T I V L | I | A V V S | V | A T G E N W | E G E R W | T | D | R G I K A | V I | I E L A A | V L I G A | V | Q A R A T | G R I T V F | A C L G V |

| | 1 | 2 | 3 | 4 | 5 | 6 | 7 | 8 | 9 | | | | | | | | | | | | | | | | | | | |
|---|---|---|---|---|---|---|---|---|---|---|---|---|---|---|---|---|---|---|---|---|---|---|---|---|---|---|---|---|
| 871 | R Q | A G | I F | R | H L | I N V | P H T | R T | R | I V | Q | G | L F K G | E G L | R L | I | L Q | L | | | | | | | | | | |

TABLE I-continued

HIV Envelope Protein Variants

| T | I | V | I | | | A | A | V |
|---|---|---|---|---|---|---|---|---|
|   |   |   |   |   |   |   | R |   |
|   |   |   |   |   |   |   | S |   |

Accordingly, based on the above examples of specific substitutions, alternative substitutions can be made by routine experimentation, to provide alternative EPVs of the present invention, e.g., by making one or more substitutions, insertions or deletions in envelope proteins or EPV's which give rise to differential immune responses.

Amino acid sequence variations in an EPV of the present invention can be prepared e.g., by mutations in the DNA. Such EPVs include, for example, deletions, insertions or substitutions of nucleotides coding for different amino acid residues within the amino acid sequence. Obviously, mutations that will be made in nucleic acid encoding an EPV must not place the sequence out of reading frame and preferably will not create complementary domains that could produce secondary mRNA structures [see, e.g., Ausubel (1995 rev.), infra; Sambrook (1989), infra].

EPV-encoding nucleic acid of the present invention can also be prepared by amplification or site-directed mutagenesis of nucleotides in DNA or RNA encoding an envelope protein or an EPV, and thereafter synthesizing or reverse transcribing the encoding DNA to produce DNA or RNA encoding an EPV [see, e.g., Ausubel (1995 rev.), infra; Sambrook (1989), infra], based on the teaching and guidance presented herein.

Recombinant viruses expressing EPV's of the present invention, recombinant EPVs, or nucleic acid vectors encoding therefor, include a finite set of EPV-encoding sequences as substitution nucleotides that can be routinely obtained by one of ordinary skill in the art, without undue experimentation, based on the teachings and guidance presented herein. For a detailed description of protein chemistry and structure, see Schulz, G. E. et al., *Principles of Protein Structure*, Springer-Verlag, New York, N.Y. (1978), and Creighton, T. E., *Proteins: Structure and Molecular Properties*, W. H. Freeman & Co., San Francisco, Calif. (1983), which are hereby incorporated by reference. For a presentation of nucleotide sequence substitutions, such as codon preferences, see Ausubel et al., eds, *Current Protocols in Molecular Biology*, Greene Publishing Assoc., New York, N.Y. (1987, 1988, 1989, 1990, 1991, 1992, 1993, 1994, 1995) (hereinafter, "Ausubel (1995 rev.)") at §§ A.1.1–A.1.24, and Sambrook, J. et al., *Molecular Cloning: A Laboratory Manual*, Second Edition, Cold Spring Harbor Laboratory Press, Cold Spring Harbor, N.Y. (1989) at Appendices C and D.

Thus, one of ordinary skill in the art, given the teachings and guidance presented herein, will know how to substitute other amino acid residues in other positions of an env DNA or RNA to obtain alternative EPVs, including substitutional, deletional or insertional variants.

Screening Assays for HIV Activity

For screening anti-HIV activity of sera or cells from an individual immunized with a vaccine of the invention, any known and/or suitable screening assay can be used, as is known in the art. For example, known HIV assays include viral infectivity assays [see, e.g., Chesebro et al., *J. Virol.* 62:3779–3788 (1988); Aldovini et al., eds., *Techniques in HIV Research* pp. 71–76 (1990)]; neutralization assays [see, e.g., Golding et al., *AIDS Res. Hum. Retrovir.* 10:633–643 (1994); Hanson., *AIDS Res. Hum. Retrovir.* 10:645–648 (1994); Laal et al., *Res. Hum. Retrovir.* 9:781–785 (1993); Hanson, *J. Acquir. Immune Defic. Syndr.* 7:211–219 (1994)]; peripheral mononuclear (PMN) cell assays [see, e.g., Arduino et al., *Antimicrob. Agents Chemother.* 37:1095–1101 (1990)]; and cytotoxic T-lymphocyte (CTL) assays [see, e.g., Hammond et al., *J. Exp. Med.* 176:1531–1542 (1992); McElrath et al., *J. Virol.* 68:5074–5083 (1994); Walker et al., *Cell. Immunol.* 119:470–475 (1989); Weinhold et al., *AIDS Res. Hum. Retrovir.* 8:1373 (1992)]. Other suitable activities, alone or in any combination, include, but are not limited to, quantitative and/or qualitative measurement of transcription, replication, translation, virion incorporation, virulence, viral yield, and/or morphogenesis. The above references are entirely incorporated herein by reference.

Specific Embodiment: Recombinant Vaccinia Virus Encoding EPV's, Polyenv Vaccines and Methods of Making and Using Thereof Overview. Recombinant vaccinia viruses (VV) expressing HIV envelope proteins (e.g., gp 41, gp 120 and/or gp 160, or a portion thereof) provide materials useful for the production and testing of mixed vaccines that induce at least one of a humoral or cellular immune response against the virus, as well as for analyses of B-cell and CTL determinants.

A polyenv vaccine of the present invention consists of a mixture of n distinct recombinant vaccinia viruses, where n is a whole number from about 4 to about 10,000 (or any range or value therein), wherein each vaccinia vector construct expresses a variant of a HIV-1 envelope protein (EPV) (e.g., gp 41, gp 120 or gp 160). The recombinant vaccinia virus functionally encodes an EPV and is prepared by recombination of wildtype VV with a plasmid. Multiple, distinct plasmids encoding EPV can be prepared by substituting one EPV encoding sequence with another, e.g., using a restriction fragment or mutagenesis.

Preparation of Recombinant Vaccinia Viruses. Methods for the preparation of individual plasmids (each expressing a unique HIV protein sequence) can utilize DNA or RNA amplification for the substitution of isolated envelope protein variant sequences into a vector (e.g., pVenv4 or pVenv1 [Hallenberger et al., *Virology* 193:510–514 (1993)], which vector encodes a known HIV envelope protein sequence (e.g., available from the NIAID AIDS Research & Reference Reagent Program, Rockville, Md.).

Methods of amplification of RNA or DNA are well known in the art and can be used according to the present invention without undue experimentation, based on the teaching and guidance presented herein. Known methods of DNA or RNA amplification include, but are not limited to polymerase chain reaction (PCR) and related amplification processes (see, e.g., U.S. Pat. Nos. 4,683,195, 4,683,202, 4,800,159, 4,965,188, to Mullis et al.; U.S. Pat. Nos. 4,795,699 and 4,921,794 to Tabor et al; U.S. Pat. No. 5,142,033 to Innis; U.S. Pat. No. 5,122,464 to Wilson et al.; U.S. Pat. No. 5,091,310 to Innis; U.S. Pat. No. 5,066,584 to Gyllensten et al; U.S. Pat. No. 4,889,818 to Gelfand et al; U.S. Pat. No. 4,994,370 to Silver et al; U.S. Pat. No. 4,766,067 to Biswas; U.S. Pat. No. 4,656,134 to Ringold) and RNA mediated amplification which uses anti-sense RNA to the target sequence as a template for double stranded DNA synthesis (U.S. Pat. No. 5,130,238 to Malek et al, with the trade name NASBA), the entire contents of which patents are herein entirely incorporated by reference.

For example, recombinant vaccinia virus constructs prepared by this route can be used for immunizations and elicitation of HIV-specific T and/or B-cell responses. Primers utilize conserved HIV sequences and thus successfully amplify env genes from many diverse HIV-1 patient samples. The basic techniques described here can similarly be used with PCR or other types of amplification primers, in order to substitute smaller or larger pieces of the env sequence from field isolates for that found in vectors encoding an HIV envelope protein. See, e.g., Ausubel; infra, Sambrook, infra.

EPV Encoding Nucleic Acids. The technique begins with the isolation of DNA from HIV infected cells and the amplification of env sequences by PCR. PCR or other amplification products provide the simplest means for the isolation of HIV sequences, but any other suitable and known methods can be used such as cloning and isolation of EPV encoding nucleic acid or proteins (see Ausubel, infra; Sambrook, infra). Enzyme restriction sites are preferably incorporated into PCR or other amplification primer sequences to facilitate gene cloning.

Isolated DNA for PCR can be prepared from multiple virus sources, inclusive of fresh or frozen whole blood from HIV+ patients and cells that have been infected in vitro with virus isolates.

In order to produce new HIV env constructs, the polymerase chain reaction (PCR) is preferably used to amplify 100–2700 base pairs (bp) of an env gene from each different HIV patient sample. The PCR primers can represent well-conserved HIV sequences which are suitable for amplifying env genes from known samples of env genes, isolated HIVs or diverse HIV patient samples. The amplified DNA preferably comprises a portion encoding 10–900 (such as 100–400, 400–600 or 600–900, or any range or value therein) amino acids of a gp120 and gp41 (both make up gp160). One or more of the envelope variable regions (V1–V5) and constant regions (C1–C5) are preferably included in the PCR products, more preferably most of the V1, C1, V2, C2, V3, C3, V4, C4, and V5 regions. In addition, amplified sequences can encode 1–200 amino acids beyond the cleavage site for gp120/gp41. Preferably, most or all of the entire env gene is amplified. Optionally, the gp160 encoding sequence amplified is missing part or all of sequences encoding the transmembrane domain and/or the cytoplasmic tail domain [see, e.g., Hallenberger et al. (1993)].

The PCR primers can be designed so that restriction enzyme sites flank the envelope gene sequence in vaccinia plasmid, such that they are incorporated into the amplified DNA products. By using well-known substitution cloning techniques, vaccinia plasmid derivatives that express envelope protein variant sequences from 1–10,000 patients can be generated by substituting a portion of the patient's EPV encoding sequence for a corresponding portion of the env sequence in the vaccinia plasmid, such as by using restriction fragments for the substitution. For example, the pVenv4 plasmid and PCR products are treated with KpnI and BsmI to obtain a sequence encoding a truncated gp160 of amino acids 1–639, which lacks both the transmembrane domain and the cytoplasmic tail domain of gp41[ see, e.g., Hallenberger et al. (1993)]

Following ligation of the PCR product and the pVenv products, bacterial host cells are transformed with the ligation mixture via any of a number of methods well-known in the art, including, e.g., electroporation, and recombinant colonies are picked and examined by sequencing.

Recombinant Vaccinia Virus Constructs Encoding HIV Envelope Proteins. The EPV encoding vaccinia is then recombined with wild type virus in a host cell and the EPV expressing virus plaques are selected and virus stocks made. The virus stocks as VVenv's each containing a different EPV encoding sequence are then mixed using at least 4–40, and up to about 10,000 different recombinant viruses, to form a polyenv vaccine of the present invention.

The recombinant vaccinia plasmids containing the EPV sequences are then optionally sequenced or screened with HIV envelope protein-specific antibodies to identify different EPVs. Sequencing by the Sanger Method dideoxy-chain termination is preferred. The procedure is preferably adapted from previously described methods [Sambrook et al. (1989), infra; United States Biochemical, *Sequenase Version 2.0—DNA Sequencing Kit*, Ninth Edition, Amersham Life Science, Inc., (1994)] and should read approximately 50–300 bp from the primer position.

Methods for the production of VV expression vectors are well-known in the art [see, e.g., Mackett, M. et al., *Proc. Natl. Acad. Sci.* (*USA*) 79:7415–7419 (1982); Panicali, D., and Paoletti, E., *Proc. Natl. Acad. Sci.* (*USA*) 79:4927–4931 (1982); U.S. Pat. No. 4,169,763; Mazzara, G. P. et al., *Methods in Enz.* 217:557–581 (1993), Ausubel et al., infra, at §§ 16.15–16.19, each of which are entirely incorporated herein by reference]. The previously described pSC11 vector [Chakrabarti, S. et al., *Mol. Cell. Biol.* 5:3403–3409 (1985)] can preferably be used to create an env-encoded plasmid, such as pVenv4.

As a viral vector, vaccinia virus has a number of useful characteristics, including capacity that permits cloning large fragments of foreign DNA (greater than 20 Kb), retention of infectivity after insertion of foreign DNA, a wide host range, a relatively high level of protein synthesis, and suitable transport, secretion, processing and post-translational modifications as dictated by the primary structure of the expressed protein and the host cell type use. For example, N-O-glycosylation, phosphorylation, myristylation, and cleavage, as well as assembly of expressed proteins, occur in a faithful manner.

Several variations of the vaccinia vector have been developed and are suitable for use in the present invention (e.g., see Ausubel et al., infra, §§ 16.15–16.19). Most commonly, after obtaining the virus stock (Ausubel, infra at § 16.16), a nucleic acid sequence encoding an EPV is placed under control of a vaccinia virus promoter and integrated into the genome of vaccinia so as to retain infectivity (Ausubel et al., infra at § 16.17). Alternatively, expression can be achieved by transfecting a plasmid containing the vaccinia promoter-controlled gene encoding an EPV into a cell that has been infected with wild-type vaccinia.

Preferably, the host cell and vaccinia vector are suitable and approved for use in vaccination of mammals and humans. These recombinant viruses are then characterized using various known methods (Ausubel et al., infra at § 16.18). In still another variation, the bacteria phage T7 RNA polymerase chain can be integrated into the genome of vaccinia so that the EPV encoding sequences will be expressed under the control of a T7 promoter, either in transfected plasma, plasmid or a recombinant vaccinia virus, will be expressed.

The use of pox virus promoters is preferred because cellular and other viral promoters are not usually recognized by the vaccinia transcriptional apparatus. A compound early/late promoter is preferably used in recombinant vaccinia for polyenv vaccines, as it is desirable to express the EPV as an antigen that is presented in recombinant vaccinia virus infected host cell in association with major histocompatibility class (MHC) I or II. Such MHC associated HIV envelope protein will then form cytotoxic T cell targets, and prime vaccinated mammals for a cytotoxic T cell response and/or a humoral response against the expressed HIV EPVs. This is because the ability of vaccinia viral vectors to induce MHC presentation in host cells for this type of antigen appears to diminish late in the infection stage. Transcripts originating early will terminate after the sequence TTTTTNT and lead to inadequate MHC presentation.

Alternatively, any such termination motifs within the coding sequence of the gene can be altered by mutagenesis if an early pox virus promoter is used, in order to enhance MHC presentation of envelope protein antigens in host cells (Earl et al., infra, 1990). To mimic vaccinia virus mRNAs, untranslated leader and 3'-terminal sequences are usually kept short, if they are used in the vaccinia plasmids incorporating HIV EPV encoding sequences.

Preferably, the plasmid used for making vaccinia constructs according to the present invention has been designed with restriction endonuclease sites for insertion of the env gene downstream of the vaccinia promoter (Ausubel et al., infra, § 16.17). More preferably, the plasmid already contains an envelope protein encoding sequence, wherein the restriction sites occur uniquely near each of the beginning and ends of the envelope protein coding sequence. The same restriction fragment of the EPV encoding sequence can then replace the corresponding sequence in the plasmid. In such cases, the major portion of the EPV encoding sequence can be inserted after removing most or all of the envelope protein encoding sequence from the plasmid.

Preferably, the resulting vaccinia construct (containing the EPV encoding sequence and the vaccinia promoter) is flanked by vaccinia DNA to permit homologous recombination when the plasmid is transfected into cells that have been previously infected with wild-type vaccinia virus. The flanking vaccinia virus DNA is chosen so that the recombination will not interrupt an essential viral gene.

Without selection, the ratio of recombinant to parental vaccinia virus is usually about 1:1000. Although this frequency is high enough to permit the use of plaque hybridization (see Ausubel et al., infra at §§ 6.3 and 6.4) or immunoscreening (Ausubel et al., infra at § 6.7) to pick recombinant viruses, a variety of methods to facilitate recombinant-virus identification have been employed. Nonlimiting examples of such selection or screening techniques are known in the art (see Ausubel et al., infra at § 16.17). Usually, the expression cassette is flanked by segments of the vaccinia thymidine kinase (TK) genes so that recombination results in inactivation of TK. Virus with a $TK^-$ phenotype can then be distinguished from those with a $TK^+$ phenotype by infecting a $TK^-$ cell line in the presence of 5-bromo-deoxyuridine (5-BrdU), which must be phosphorylated by TK to be lethally incorporated into the virus genome. Alternatively or additionally, recombinant viruses can be selected by the co-expression of a bacterial antibiotic resistant gene such as ampicillin (amp) or guanine phosphoribosyl transferase (gpt). As a further example, co-expression of the *Escherichia coli* lac Z gene allows co-screening of recombinant virus plaques with Xgal (Ausubel, infra, § 16.17).

The recombinant vaccinia viruses expressing an EPV of the present invention can be optionally attenuated or inactivated according to known methods, such as by heat, paraformaldehyde treatment, ultraviolet irradiation, propriolactene treatment, hybrid or chimera formation or by other known methods [see, e.g., Zagury et al., *Nature* 332:728–731 (1988); Ito et al., *Cancer Res.* 50:6915–6918 (1990); Wellis et al., *J. Immunol.* 99:1134–9 (1967); D'Honcht, *Vaccine* 10 (Suppl.):548–52 (1992); Selenka et al., *Arch. Hyg. Bakteriol.* 153:244–253 (1969); Grundwald-Bearch et al., *J. Cancer Res. Clin. Oncol.* 117:561–567 (1991); the contents of which are entirely incorporated here by reference]. For example, heat inactivation at 60° C. will reduce virus titer considerably. Such attenuation techniques are safety tested, as incomplete inactivation might result in patient death [Dorozynski and Anderson, *Science* 252:501–502 (1991)].

Such attenuated or inactivated recombinant vaccinia is to be used where the patient may have a compromised immune system as complications or death can occur when live vaccinia is administered.

Pharmaceutical Compositions

Pharmaceutical preparations of the present invention, suitable for inoculation or for parenteral or oral administration, include a polyenv recombinant virus vaccine comprising of at least 4, and up to about 10,000, preferably 4 to about 1000, and more preferably about 10 to about 100 different recombinant viruses, in the form of a cell lysate, membrane-bound fraction, partially purified, or purified form. Preferably, the polyenv vaccine comprises recombinant virus containing cell lysate (or membrane-bound fractions thereof) that further comprise EPV proteins already expressed by the recombinant viruses. The inclusion of the expressed EPVs is now discovered to enhance the primary antibody response.

The polyenv vaccine composition can be in the form of sterile aqueous or non-aqueous solutions, suspensions, or emulsions, and can also contain auxiliary agents or excipients which are known in the art. Each of the at least about 4–40 to 10,000 different viruses encode and express a different EPV, as presented herein. EPVs encoding DNA can be selected to represent EPVs existing in a specific isolated community of AIDS patients. For example, a vaccine could represent sequences from Memphis, Tenn. and be targeted for use in Memphis, Tenn. Vaccines designed to represent geographically restricted areas can also be useful for use in communities outside of the targeted community.

Alternatively, EPVs encoding DNAs can be selected to represent geographically distant communities, cities or countries, such as clades. For example, multiple clones can be represented in one polyenv vaccine. A polyenv vaccine composition can further comprise immunomodulators such as cytokines which accentuate an immune response to a viral infection. See, e.g., Berkow et al., eds., *The Merck Manual*, Fifteenth Edition, Merck and Co., Rahway, N.J. (1987); Goodman et al., eds., *Goodman and Gilman's The Pharmacological Basis of Therapeutics*, Eighth Edition, Pergamon Press, Inc., Elmsford, N.Y. (1990); *Avery's Drug Treatment: Principles and Practice of Clinical Pharmacology and Therapeutics*, Third Edition, ADIS Press, LTD., Williams and Wilkins, Baltimore, Md. (1987); and Katzung, ed. *Basic and Clinical Pharmacology*, Fifth Edition, Appleton and Lange, Norwalk, Conn. (1992), which references and references cited therein, are entirely incorporated herein by reference as they show the state of the art.

As would be understood by one of ordinary skill in the art, when a polyenv vaccine of the present invention is provided to an individual, it can be in a composition which can further comprise at least one of salts, buffers, adjuvants, or other substances which are desirable for improving the efficacy of the composition. Adjuvants are substances that can be used to specifically augment at least one immune response. Normally, the adjuvant and the composition are mixed prior to presentation to the immune system, or presented separately, but into the same site of the being immunized. Adjuvants can be loosely divided into several groups based upon their composition. These groups include oil adjuvants, mineral salts (for example, $AlK(SO_4)_2$, $AlNa(SO_4)_2$, $AlNH_4(SO_4)$, silica, kaolin, and carbon), polynucleotides (for example, poly IC and poly AU nucleic acids), and certain natural substances (for example, wax D from *Mycobacterium tuberculosis*, substances found in *Corynebacterium parvum*, or *Bordetella pertussis*, and members of the genus Brucella). Among those substances particularly useful as adjuvants are the saponins (e.g., Quil A., Superfos A/S, Denmark). Examples of materials suitable for use in vaccine compositions are disclosed, e.g., in Osol, A., ed., *Remington's Pharmaceutical Sciences*, Mack Publishing Co., Easton, Pa. (1980), pp. 1324–1341, which reference is entirely incorporated herein by reference.

A pharmaceutical polyenv vaccine composition of the present invention can further or additionally comprise at least one antiviral chemotherapeutic compound. Non-limiting examples can be selected from at least one of the group consisting of gamma globulin, amantadine, guanidine, hydroxy benzimidazole, interferon-α, interferon-β, interferon-γ, interleukin-16 (IL-16; Kurth, *Nature*, Dec. 8, 1995); thiosemicarbarzones, methisazone, rifampin, ribvirin, a pyrimidine analog (e.g., AZT and/or 3TC), a purine analog, foscarnet, phosphonoacetic acid, acyclovir, dideoxynucleosides, a protease inhibitor (e.g., saquinavir (Hoffmann-La Roche); indinavir (Merck); ritonavir (Abbott Labs); AG 1343 (Agouron Pharmaceuticals); VX-2/78 (Glaxo Wellcome)); chemokines, such as RANTES, MIP1α or MIP1β [*Science* 270:1560–1561 (1995)] or ganciclovir. See, e.g., Richman: *AIDs Res. Hum. Retroviruses* 8: 1065–1071 (1992); *Annu Rev Pharmacol Toxico* 33: 149–164 (1993); *Antimicrob Agents Chemother* 37: 1207–1213 (1993); *AIDs Res. Hum. Retroviruses* 10: 901 (1994): Katzung (1992), infra, and the references cited therein on pages 798–800 and 680–681, respectively, which references are herein entirely incorporated by reference.

Pharmaceutical Uses

The administration of a polyenv vaccine (or the antisera which it elicits) can be for either a "prophylactic" or "therapeutic" purpose, and preferably for prophylactic purposes. When provided prophylactically, the live polyenv vaccine composition is provided in advance of any detection or symptom of HIV infection or AIDS disease. The prophylactic administration of the compound(s) serves to prevent or attenuate any subsequent HIV infection.

When provided therapeutically, the polyenv vaccine is provided upon the detection of a symptom of actual infection. The administration of a live polyenv vaccine after HIV infection is provided only where the patient's immune system is determined to be capable of responding to administration of the live polyenv vaccine without substantive risk of unsuitable complications or death, where the administration of a live virus is provided in the required dosage that serves to attenuate any actual HIV infection.

Alternatively, where the patient's immune response is compromised, therapeutic administration preferentially involves the use of an attenuated or inactivated polyenv vaccine composition where the recombinant viruses are attenuated or inactivated, as presented above. See, e.g., Berkow (1987), infra, Goodman (1990), infra, Avery (1987), infra and Katzung (1992), infra, Dorozynski and Anderson, *Science* 252:501–502 (1991) which are entirely incorporated herein by reference, including all references cited therein.

A composition is said to be "pharmacologically acceptable" if its administration can be tolerated by a recipient patient. Such an agent is said to be administered in a "therapeutically or prophylactically effective amount" if the amount administered is physiologically significant. A vaccine or composition of the present invention is physiologically significant if its presence results in a detectable change in the physiology of a recipient patient, preferably by enhancing a humoral or cellular immune response to an HIV.

The "protection" provided need not be absolute, i.e., the HIV infection or AIDS disease need not be totally prevented or eradicated, provided that there is a statistically significant improvement relative to a control population. Protection can be limited to mitigating the severity or rapidity of onset of symptoms of the disease.

Pharmaceutical Administration

A vaccine of the present invention can confer resistance to one or more strains of an HIV. The present invention thus concerns and provides a means for preventing or attenuating infection by at least one HIV strain. As used herein, a vaccine is said to prevent or attenuate a disease if its administration to an individual results either in the total or partial attenuation (i.e. suppression) of a symptom or condition of the disease, or in the total or partial immunity of the individual to the disease.

At least one polyenv vaccine of the present invention can be administered by any means that achieve the intended purpose, using a pharmaceutical composition as described herein.

For example, administration of such a composition can be by various parenteral routes such as subcutaneous, intravenous, intradermal, intramuscular, intraperitoneal, intranasal, transdermal, or buccal routes. Subcutaneous administration is preferred. Parenteral administration can be by bolus injection or by gradual perfusion over time. See, e.g., Berkow (1987), infra, Goodman (1990), infra, Avery (1987), infra, and Katzung (1992), infra, which are entirely incorporated herein by reference, including all references cited therein.

A typical regimen for preventing, suppressing, or treating a disease or condition which can be alleviated by a cellular immune response by active specific cellular immunotherapy, comprises administration of an effective amount of a vaccine composition as described is above, administered as a single treatment, or repeated as enhancing or booster dosages, over a period up to and including one week to about 24 months.

According to the present invention, an "effective amount" of a vaccine composition is one which is sufficient to achieve a desired biological effect, in this case at least one of cellular or humoral immune response to HIV. It is understood that the effective dosage will be dependent upon the age, sex, health, and weight of the recipient, kind of concurrent treatment, if any, frequency of treatment, and the nature of the effect desired. The ranges of effective doses provided below are not intended to limit the invention and represent preferred dose ranges. However, the most preferred dosage will be tailored to the individual subject, as is understood and determinable by one of skill in the art, without undue experimentation. See, e.g., Berkow (1987), infra, Goodman (1990), infra, Avery (1987), infra, Ebadi, *Pharmacology*, Little, Brown and Co., Boston, Mass. (1985), and Katsung (1992), infra, which references and references cited therein, are entirely incorporated herein by reference.

Generally speaking, the dosage for a human adult will be from about $10^5$–$10^9$ plaque forming units (pfu)/kg or colony forming units (CFU)/kg per dose, with $10^6$–$10^8$ preferred. Whatever dosage is used, it should be a safe and effective amount as determined by known methods, as also described herein.

Subjects

The recipients of the vaccines of the present invention can be any mammal which can acquire specific immunity via a cellular or humoral immune response to HIV, where the cellular response is mediated by an MHC class I or class II protein. Among mammals, the preferred recipients are mammals of the Orders Primata (including humans, chimpanzees, apes and monkeys). The most preferred recipients are humans. The subjects preferably are infected with HIV or provide a model of HIV infection [e.g., Hu et al., *Nature* 328:721–723 (1987)], which reference is entirely incorporated herein by reference.

Having now generally described the invention, the same will be more readily understood through reference to the following examples, which are provided by way of illustration, and are not intended to be limiting of the present invention.

EXAMPLES

Example 1

Preparation of Vaccinia Virus Vectors for HIV Env Protein Expression

Nomenclature. For purposes of reference, a recombinant vaccinia virus construct is alternatively referred to herein as a VVenv construct, with specific vaccinia virus constructs being designated according to a patient, or to a depository (e.g., ATCC br the GenBank source of the env DNA in the construct). For example, VVenv-Doe would refer to a vaccinia virus vector construct having env sequences from patient Doe, and VVenv-U28305 would refer to a vaccinia virus vector having the env sequences found in GenBank accession No. U28305.

The polyenv vaccine consists of 4–100 distinct recombinant vaccinia viruses, each of which expresses a unique HIV-1 envelope protein. For purposes of reference, each individual virus is designated as VVenv, and the final virus mixture is referred to as polyenv.

The preparation of each VVenv uses the plasmid designated pVenv4 and a wildtype vaccinia virus designated NYCDH, described below. For additional details, see Ryan et al., "Preparation and Use of Vaccinia Virus Vectors for HIV Protein Expression and Immunization," in *Immunology Methods Manual*, Lefkovits, ed., Academic Press (1996).

Vectors and Host Cells. The previously described pSC11 vector [Chakrabarti, S. et al., *Mol. Cell. Biol.* 5:3403–3409 (1985)] can be used for the recombination of multiple HIV genes into the VV genome. Elements of the pSC11 plasmid include the lacZ gene (a reporter gene by which transformed bacteria and VV recombinants can be easily identified as those having β-galactosidase activity), a portion of the gene encoding thymidine kinase (TK), and an ampicillin resistance gene (amp). Genes cloned into pSC11 are inserted into the VV genome by homologous recombination between the TK gene of the wildtype virus and the portions of the TK gene contained in pSC11. Insertion of plasmid DNA into the viral TK locus inactivates the viral gene so that recombinant viruses can be readily selected from the background of $TK^+$ virus by growth in bromodeoxyuridine (BUdR). In order for recombinant $TK^-$ virus to survive this selection, they must be grown in cells which do not supply an active TK enzyme, such as the $TK^-$143 cell line, which is a TK-deficient derivative of the human cell line R970-5, an osteosarcoma cell line (Rhim, J. S. et al., *Int. J. Cancer* 15:23–29 (1975)] that supports the growth of VV [Weir et al., infra (1982)]. The production of HIV gene segment expression can be by full gene insertion into the SmaI site of the pSC11 vector. Full length genes can be expressed under the control of the P7.5K promoter.

As an alternative to the cloning of complete HIV genes, one can substitute partial gene sequences for HIV genes that have already been cloned into pSC11. For example, a construct termed pVenv1 was prepared from pSC11 and expresses the BH10 HIV envelope protein (env) gene [Hallenberger et al., infra, (1993); Kilpatrick et al. *J. Biol. Chem.* 262:116–121 (1987)]. The construct can be used as a parent vector to substitute and express variable envelope protein regions from field HIV isolates. Similarly, a vector termed pVenv4 was constructed from pSC11 to express a BH10 env protein, truncated to exclude the transmembrane and cytoplasmic tail domain encoding gp41 sequences while retaining the oligomerization domain [Hallenberger et al. (1993), infra]. As can be appreciated by the skilled artisan, the term "oligomerization domain" is used functionally, to refer to a portion of gp41 that permits oligomerization of env proteins, i.e., there is sufficient structure for oligomerization. The pVenv4 vector encodes a truncated gp160 (also: gp160t, gp140) that was discovered to form a tertiary structure that is similar to that of the processed gp41/gp120 oligomer (dimer, trimer or tetramer) as is present at the cell surface of HIV infected cells. This tertiary structure is maintained in both secreted and membrane associated form [Hallenberger et al., (1993)]. This vector is preferably used as a parent vector for the substitution of alternative isolated env sequences.

In this Example, the preparation of each VVenv construct involves the use of a pVenv4 and a wildtype vaccinia virus NYCDH, and appropriate host cells, as is described in detail below.

pVenv4. The pVenv4 vector was previously prepared by the insertion of an HIV-1-envelope coding sequence into the pSC11 vaccinia virus recombination vector [Hallenberger, et al., *Virology* 193:510–514 (1993); Chakrabarti et al., *Mol. Cell Biology* 5:3403–3409 (1985)]. The HIV-1 sequence was derived from a laboratory stock of live virus. The sequence was named "BH10" [Ratner et al., *Nature* 313:277–284 (1985)]. With PCR techniques unique envelope sequences from HIV-1 infected patients may be amplified and substituted into the BH10 env sequence to create new vectors. For example, the following primers might be used for PCR.

(A) Sense, Position 5785 (SEQ ID NO:1): AGCAGAA-GACAGTGGCAATGAGAGTGA.

(B) Antisense, Position 7694 (SEQ ID NO:2): CCACTC-CATCCAGGTCATGTTATTCCAAAT.

(C) KpnI-Sense, position 5903 (SEQ ID NO:3): GTGGGTCACAGTCTATTATGGGGTACCTGTGT.

(D) BsmI-Antisense, position 7659 (SEQ ID NO:4): CCAGAGATTTATTACTCCAACTAGCATTCCAAGG.

(E) (optional) DraIII-Sense, position 6153 (SEQ ID NO:5): CCATGTGTAAAATTAACCCCACTCTGTG.

(F) (optional) Bsu36I-Anti-sense, position 6917 (SEQ ID NO:6): TACAATTTCTGGGTCCCCTCCTGAGG.

These primers are written 5 to 3. Restriction sites are underlined (numbered positions are based on the BH10 sequence [Ratner et al., Nature 313:277–284 (1985)].

PCR Strategy. In order to produce new HIV-1 env constructs, the polymerase chain reaction (PCR) is used to amplify 1800 base pairs (bp) of envelope gene from forty different HIV-1 patient samples. The PCR primers represent well-conserved HIV-1 sequences and thus successfully amplified env genes from many diverse HIV-1 patient samples. The amplified DNA encompasses the entire gp120 protein except for approximately 10 highly conserved amino acids at the protein's amino terminus. All. envelope variable regions (V1–V5) are included in the PCR products. In addition, amplified sequences encode approximately 100 amino acids beyond the cleavage site for gp120/gp41.

The PCR primers carrying the restriction enzyme sites for KpnI and BsmI, which flank the BH10 envelope gene sequence in pVenv4, are incorporated into the amplified DNA products.

First Round PCR. In a 500 μl microcentrifuge tube, mix:

1 μl Primer A (SEQ ID NO: 1), 300 ng/μl;

1 μl primer B (SEQ ID NO: 2), 300 ng/μl;

2.5 μl 10 mM of each of 4 dNTPs;

1 μg DNA;

10 μl 10X PCR buffer; and

HPLC H20 to 99 μl

Vortex taq stock and dispense 1 μl to PCR reaction. Mix well. Overlay with mineral oil.

Run on a thermal-cycler as follows:

Incubate 95° C., 3 minutes to melt DNA.

Run 40 cycles: 95° C., 1 minute; 45° C., 2 minutes; 72° C., 3.5 minutes.

Second Round PCR: Prepare PCR reaction as above, but with primers C and D (SEQ ID NOS:3 and 4, respectively) and without the DNA. Bring the final solution to 95 μl. Overlay with mineral oil. With a plugged tip, remove 5 μl from the first PCR reaction (from below the oil). Mix the sample into the second reaction, below oil layer and begin cycles as before. Thirty cycles is usually appropriate. It can be desirable to monitor the product by removing 2 μl for gel analysis after each 10 cycles until a clear band is identified of approximately 1800 bp.

By using well-known substitution cloning techniques, pVenv4 derivatives that express an env sequence from one of the 40 patients, instead of the BH10 envelope sequence, were generated. Briefly, the pVenv4 plasmid and PCR products are next cut with KpnI and BsmI, and the cut pVenv4 was run on an agarose gel and the large fragment isolated. The small fragment (1800 bp fragment) of BH10 env was discarded. The cut PCR product was also isolated and ligated to the large pVenv4 fragment to create a chimeric envelope sequence, now containing 1800 bp of the variant env from the patient DNA. Following ligation of the PCR product and the pVenv products, bacterial host cells are transformed with the ligation mixture via any of a number of methods well-known in the art, including, e.g., electroporation, and recombinant colonies are picked and examined by sequencing.

Plasmid pVenv4 or recombinants made with pVenv4 facilitates the insertion of genes into the vaccinia virus genome by homologous recombination between the thymidine kinase (Tk) gene of the wildtype virus and the Tk sequences within the plasmid. Insertion of pVenv4 DNA into the viral Tk locus yields a vaccinia virus with the HIV-1 envelope gene expressed under the control of the P7.5K early/late promoter. The virus is attenuated in growth activity due to the disruption of the Tk locus. An additional element of pVenv4 is the lacZ gene that encodes β-galactosidase activity, lacZ activity can be used to select vaccinia virus recombinants (see below).

The envelope gene expressed by pVenv4 is truncated to exclude the transmembrane/C-terminal gp41 sequence. The vector is expressed as an oligomeric structure that is found within cells and in secreted form.

Vaccinia virus-NYCDH. Each new, substituted plasmid is individually recombined with wildtype vaccinia virus NYCDH. This virus was obtained from A.T.C.C. (Accession No. VR-325) and was plaque-purified prior to use (Buck, C., and Paulino, M. S., eds., *American Type Culture Collection Catalogue of Animal Viruses and Antisera, Chlamydiae and Rickettsiae,* 6th Ed., American Type Culture Collection, Rockville, Md. (1990), p. 138).

Bacterial host cells. The plasmid may be grown on any suitable host, as known in the art [see, e.g., Ausubel, infra (1995 rev), §§ 16.15–16.19]. A non-limiting example is DH5α cells.

TK-deficient cells. The transformation and vaccinia virus substitution is done on the human $Tk^{-}$143B cell line, which is a TK-deficient derivative of the human cell line R970-5, an osteosarcoma cell line [Rhim et al. (1975), infra] that supports the growth of VV [Weir et al. (1982), infra]. Each vaccinia virus recombinant containing a unique HIV env gene sequence is selected based on expression of the lacZ gene (Virus plaques are overlayed with Bluo-gal and selected for β-galactosidase activity as judged by the development of a blue color). Two rounds of PCR can be performed.

Example 2

Preparation of Polyenv Vaccine

Vero Cells. The final manufacturing step is to grow n VVenv constructs on Vero cells newly purchased from the A.T.C.C. (Accession No. CCL81 or X38) and cloned and expanded for virus growth. The Vero cell line has been approved by the World Health Organization for vaccine development [Hay, R., et al., eds., *American Type Culture Collection Catalogue of Cell Lines and Hybridomas,* 7th Ed., American Type Culture Collection, Rockville, Md. (1992), page 48].

Vero cells are grown with Dulbecco's Modified Eagles Medium (Bio-Whittaker), a glutamine supplement (Bio-Whittaker) and heat-inactivated fetal calf serum (Hyclone, Inc.). Alternatively, serum-free media can be used. Each VVenv construct is inoculated onto a separate confluent layer of Vero cells and harvested when cells demonstrate cytopathic effects due to virus infection. Cell extracts are washed extensively with PBS (Bio-Whittaker) after harvest and before freezing. The cells are then broken open by freeze-thawing, sonication or centrifuging at low speed in a centrifuge (optional). Aliquots of supernatant are then stored at −70° C. Envelope protein is present in the lysate at sufficient concentrations to elicit HIV envelope protein-specific antibody (as detectable by ELISA) in mammal models, even if VV is attenuated, e.g., prep is heated to 60° C., 1 hr.

The Vaccine Product. Each virus (VVenv construct) stock from Vero cells is individually frozen and subsequently titered and safety tested. After tests have been completed, aliquots of each virus are mixed to yield a stock vaccine of $10^8$ total pfu/ml ("pfu" stands for plaque-forming units). If 40 VVenv constructs are utilized, each VVenv is preferably equally represented, each VVenv used at a titer of $2.5 \times 10^6$ pfu/ml in the vaccine product. This should yield $1 \times 10^8$ total pfu.

Evaluation of Polyenv Vaccine

Mice. Mice can be infected with an intraperitoneal injection of $1\times10^7$ pfu env-expressing VV. Antibody can be identified by HIV ELISA or neutralization assays, as described above, three weeks after VV injections.

Prior to manufacture of the polyenv vaccine for human use, a similar group of viruses has been prepared for the purpose of vaccine testing in mice. These viruses were administered to mice either by the intraperitoneal or subcutaneous route. We then tested serum HIV-1-specific antibody serum was tested for activity in an enzyme-linked immunosorbant assay (ELISA). The assay involved the plating of whole, disrupted HIV-1 ($HTLV_{IIIB}$) on ELISA plates and the blocking of plates with bovine serum albumin. Serum samples were then added at dilutions of 1:100, 1:1,000 and 1:10,000 in phosphate-buffered saline. The assay was developed with an alkaline-phosphatase-conjugated goat-anti-mouse immunoglobulin antibody and p-nitrophenyl phosphate. The color reaction was stopped with a sodium hydroxide solution, and the optical density reading was taken on an ELISA plate reader at 405 nm.

As shown in FIG. 2, a single inoculation with cell lysate preparation of $10^6$–$10^7$ pfu vaccinia virus (containing a single HIV-1/envelope protein encoding sequence and membrane bound expressed envelope protein) elicited a strong antibody response toward HIV-1 that was sustained throughout the experimental time course of six months. Such an antibody response was significantly higher than previously reported with other immunizations. This high antibody response may be attributed to the presence of membrane bound envelope protein in a vaccine preparation. As shown in FIG. 3, these responses were dose dependent. Lower responses were seen in mammals given a dose of $10^6$ pfu than in mammals given a dose of $10^7$ pfu.

Mixtures of vaccinia viruses expressing different HIV-1 envelope proteins were also prepared. When mice received $10^7$ pfu of a mixture of five viruses, their responses were essentially identical in magnitude to responses generated against $10^7$ pfu of a single vaccinia virus recombinant (FIG. 4). The mixing of numerous env-expressing vaccinia viruses in high numbers has not been reported, and is expected to provide broad spectrum of neutralizing antibody.

Humans. Tests of the mixed virus stock are performed prior to clinical trials, the first of which will be for the purpose of dose escalation and safety testing.

The clinical trials will be a dose escalation study involving the assembly of four volunteer groups. Each group receives one of the following vaccine doses:

(1) $2\times10^4$ pfu
(2) $2\times10^5$ pfu
(3) $2\times10^6$ pfu
(4) $2\times10^7$ pfu Each volunteer receives the mixed virus vaccine in 0.5 ml saline, administered by a subcutaneous injection.

Example 3

Induction of Primary Isolate Neutralizing Immunity with a Multi-envelope, Vaccinia Virus-based Hiv-1 Vaccine in Chimpanzees The population of HIV-1 isolates is armed with a sophisticated array of envelope proteins. Env proteins are the sole virally-encoded external proteins and targets of neutralizing antibody activity, yet antibodies elicited toward one isolate will not necessarily neutralize another. For this reason, we have prepared an HIV-1 vaccine cocktail, PolyEnv, expressing numerous Env proteins. Vaccine production began with the preparation of thirty distinct VV-recombinants, each expressing a distinct Env protein. VVenv were then tested, individually and in combination (PolyEnv) in a chimpanzee model. Four chimpanzees were immunized subcutaneously with three injections of single VVenv (Chimps 1 and 2) or PolyEnv (Chimps 3 and 4) followed by one intramuscular injection with recombinant gp120/gp41 protein in alum. Safety was demonstrated in all four animals, only two of which showed signs of ulceration at the injection site. Serum samples were monitored by numerous tests for HIV-binding and neutralization. The antibodies of chimps 3 and 4 demonstrated the highest quality of antibody activity. Neutralizing function was demonstrated both against a laboratory isolate and a primary isolate of HIV-1, neither of which were specifically represented in the vaccine. Thus, the priming of lymphocytes with mixed env proteins thus provides a promising method by which high-quality antibodies may be elicited against diverse HIV-1.

Materials and Methods pVenv4, a VV recombination vector. pVenv4 was previously prepared by the introduction of a stop codon into the BH10-env sequence, and the insertion of the modified BH10 envelope gene (env) into pSC11. pVenv4 expressed an Env protein product that was truncated at amino acid 640, and was capable of both secretion and oligomerization. The production of a recombinant VV, Vvenv4, expressing this truncated BH10 Env protein has been described previously [Hallenberger et al., *Virology* 193:510–514 (1993)].

PCR for the amplification of env sequences from HIV-1-infected individuals. PCR was used to amplify HIV env sequences. Generally, samples derived from the blood of HIV-1 infected individuals, taken at first diagnosis for HIV. Other samples were from individuals with clinical symptoms of AIDS, or from products provided by the AIDS research and reference reagent repository. For blood samples, DNA was first prepared by the dropwise addition of blood or infected cells into an SDS-based cell lysis buffer and incubation at 65 degrees C. for 30 min. Pronase was added at a concentration of 0.5 mg/ml and the lysate was further incubated at 45 degrees C. overnight. Two phenol extractions were followed by ethanol precipitation, and resuspension of DNA in water.

Two rounds of PCR were performed with all DNA samples by standard methods. Primer sequences were chosen based on the published BH10 sequence [Ratner et al., *Nature* 13:277–284 (1985)]. To obtain fragments including sequences from all variable regions and a portion of gp41, PCR primers as described in Example 1 were used. PCR products were subsequently cloned by substitution into the pVenv4 vector using standard methods. Sequencing was performed on the novel plasmids by use of the Sanger method and primer ccatgtgtaaaattaaccccactctgtg (SEQ ID NO:5).

Preparation of VVenv. Novel VV recombinants (VVenv) were prepared by the transfection of VV (NYCDH, ATCC)-infected cells with the newly substituted recombination plasmids (see above). Transfectam (Promega) and Lipofectamine (Gibco, BRL) were used to facilitate transfection, following the manufacturer's recommendations. VV were then plaque purified.

Immunizations. VVenv-infected cell lysates were administered to chimpanzees with subcutaneous injections. VVenv were either used singly, or in combination. The total quantities of VV by pfu were similar in each injection (approximately $10^7$ pfu) per animal. Intramuscular injections were with a mixture of approximately 40 micrograms gp120 (Cat # 12101, Intracel, Cambridge, Mass.), 20 micrograms of gp41 (Cat #036001, Intracel) and 500 micrograms alum (Rehsorptar Aluminum hydroxide Adsorptive Gel, Intergen Co., Purchase, N.Y.) per inoculum.

ELISAs. Five ELISAs were performed as follows: ELISA #1 The Abbott clinical ELISA was purchased from Abbott Laboratories and performed as recommended by the manufacturers (HIVAB HIV-1/HIV-2 (rDNA) EIA, Abbott Laboratories, Abbott Park, Ill.). ELISA #2: ELISAs were performed by plating recombinant Mn-gp160 (Quality Biological, Inc. Gaithersburg, Md.) at one microgram/ml. Plates were blocked and tests were performed with three-fold serial dilutions of sera. Plates were then washed and scored with alkaline phosphatase-conjugated anti-human IgG. ELISA 3: ELISA plates were coated with one microgram/ml of LAI-gp120 (CHO-derived protein, Intracel). Serum samples were plated after a 1:100 dilution and scored with alkaline phosphatase-conjugated anti-human IgG1 (Mouse anti-human IgG1-AP, cat #9050-04, Southern Biological Associates, Inc., Birmingham, Ala.) and p-nitrophenyl phosphate. O.D. readings were taken at 405 nm. ELISA #4: The ELISA was performed as in assay #3, except that plates were coated with one microgram/ml of IIIB-gp120 (baculovirus-derived protein, Intracel, cat#12001, Cambridge, Mass.). ELISA#5: The ELISA was performed as in assay #3, except that plates were coated with one microgram/ml of IIIB virus lysate (Organon Teknika Co. Durham, N.Y).

Neutralization assays. Neutralization assays were performed with laboratory or primary isolates [Montefiori et al., *J. Clin. Microbiol.* 26:231–237 (1988); Montefiori et al., *Journal of Infectious diseases* 173:60–67 (1996)]. Laboratory isolates: Virus was mixed with a 1:20 dilution of each serum sample, and plated on MT-2 or CEM-x174 cells. Neutral red stain was used to assess the viability of cells. A 35–40% reduction in cell death compared to control cultures was defined as positive deflection. Primary Isolates: Virus was mixed with a 1:4 dilution of each serum sample, and plated on PHA-stimulated PBMC. Assays were scored for p24. A reduction of infectivity of at least 75% compared to control cultures was required for a positive score.

Results

Preparation of novel VVenv recombinant vaccinia viruses. In order to prepare new VV recombinants (VVenv), each expressing a unique HIV-1 Env protein, DNA was first isolated from HIV-1 samples. Most DNAs were from the blood of individuals who had shown no outward signs of disease and were likely at first diagnosis for HIV-1 infection. Additional DNAs were from AIDS patients or from viruses provided by the AIDS Research and Reference Reagent Repository. PCR was performed with primer pairs encompassing KpnI and BsmI restriction sites. Fragments were then substituted into the pVenv4 vector portrayed in FIG. 5 (pVenv4 originally expressed a truncated HIV-1 protein, BH10) at KpnI and BsmI restriction sites. In this way, gp120 (V1–V5) and gp41 sequences from BH10 were replaced by respective sequences in PCR products. With each substituted plasmid, a new VV recombinant virus (VVenv) was prepared.

This method provided a simple means by which a great diversity of Env sequences could be incorporated into unique VV recombinants (VVenv). Interestingly, the majority of sequences were productive, suggesting that Env sequences in proviral genomes (from which most PCR products derived) were rarely defective. Enormous diversity exists among the VVenv used in the vaccine mixture.

Immunization of chimpanzees with single or mixed VVenv. Four chimpanzees were used for the testing of single and mixed VV-recombinant vaccines. The schedule of immunizations are shown in Table 2. The first three injections contained VV while the last injection contained a combination of gp120, gp41 and alum, given intramuscularly. Chimps 1 and 2 received only one vaccinia virus and respective envelope protein, given in each of the first three injections. Chimps 3 and 4 received a mixture of 10 recombinant VV (and respective Env in the first injection), ten additional Env in the second injection, and 10 additional, unique Env in the last immunization, yielding a total of 30 distinct vectors prior to the protein boost. All chimps received similar quantities of total vaccinia virus in plaque forming units and similar quantities of total recombinant proteins.

TABLE 2

Immunization schedule for chimpanzees with mixed VV recombinants

| | Date | Injection |
|---|---|---|
| Chimps 1 and 2: | 1/9/96 | VV (Env #1) |
| | 4/16/96 | VV (Env #1) |
| | 6/11/96 | VV (Env #1) |
| | 7/30/96 | recombinant gp120 and recombinant gp41 + alum. |
| Chimps 3 and 4: | 1/9/96 | VV (Env #1–10) |
| | 4/16/96 | VV (Env #11–20) |
| | 6/11/96 | VV (Env #21–30) |
| | 7/30/96 | recombinant gp120 and recombinant gp41 + alum. |

Recombinant VVenv may be administered without lesion eruption. All four chimps were monitored for signs of systemic disease and lesion formation at the site of infection. Animals were analyzed on a daily basis for diarrhea, rhinorrhea, coughing, sneezing, rapid respiration, lethargy, restricted movement and loss of appetite. None of these signs were evident in any animal at any time. Photographs taken of the injection sites at regular intervals after the first VV immunization showed swelling evident in all four animals. Mild lesions appeared at the injection sites on chimps 1 and 3 typifying a smallpox vaccination, while no lesions were evident on chimps 2 and 4. No disease symptoms, swelling or lesions were evident in the second, third or fourth injections in any animal, demonstrating that VV-specific immunity had been elicited by the first inoculation.

Injections of VVenv followed by protein booster immunizations yielded ELISA-positive antibody. HIV-specific antibodies were monitored during the immunization scheme by five different ELISAs. ELISAs were used to measure the relative quality, rather than absolute quantity of antibodies in each animal. In most cases, tests were with virus fragments that lacked the three-dimensional and oligomeric structure typical of native Env. In these cases, ELISAs would be expected to bind only a subset of HIV-specific antibodies. Results obtained with the Abbott ELISA are shown in FIG. 6. Chimp 3 exceeded the cut-off for positivity after the first VV immunization, while chimp 4 exceeded the cut-off after the second VVenv immunization. The responses of chimps 3 and 4 at the end of the immunization scheme far exceeded those of chimps 1 and 2. In ELISA #2 with MN gp160, chimp 3 was the only high responder. This response occurred prior to the protein boost, and was not perturbed by the booster injection. The response to CHO-LAI bound to an ELISA (ELISA #3) plate using the same antigen as that used for the purified protein boost, showed only chimp 3 responded strongly. In ELISA #4 with IIIB-gp120 plate bound, Chimp 2 showed a high background and, perhaps due to the high background, the highest response value of all animals. Responses to the fifth ELISA, Organon Technika IIIB virus lysate, were positive with sera from all four animals.

Neutralization responses toward primary and laboratory isolates. Neutralization assays were performed with sera from each animal against laboratory and primary isolates. The first assay was performed on a T-cell line, while the latter assay was performed on sero-negative PHA-stimulated PBMC. In all cases, the isolates did not match those represented in the HIV-1 vaccines.

As demonstrated in Table 3, samples from chimp 2, chimp 3 and chimp 4 yielded a positive deflection (35–40% inhibition in virus growth) against the MN laboratory isolate in T cells. Assays with two other laboratory viruses (one IIIB [Lockey et al., *Aids Res Hum Retroviruses* 12:1297–1299 (1996)] and one SF2 stock) did not score positively with any sample. The results of neutralization assays [Montefiori et al., 1988, supra; Montefiori et al., 1996, supra] with four primary isolates tested on PHA-stimulated PBMC are shown. Virus is considered difficult to neutralize in these assays, as patient sera often yield negative results, even when 1:2 dilutions are used [Fenyo et al., *AIDS* 10:S97–S106 (1996); Moore and Ho, *AIDS* 9:S117–S136 (1995); Montefiori et al., 1996, supra]. Interestingly, a 1:4 dilution of chimp 4 serum was able to neutralize one of the test primary isolates. The situation differed from the experiences of others with Env vaccines, as in most previous cases, sera from Env-immunized individuals have yielded negative results in primary isolate neutralization assays [Steele, *Journal of NIH research* 6:40–42 (1994); Moore, *Nature* 376:115 (1995)].

TABLE 3

Neutralization by chimp antisera of viruses not specifically represented in vaccine

| Isolate | Chimp 1 | Chimp 2 | Chimp 3 | Chimp 4 |
| --- | --- | --- | --- | --- |
| Laboratory strain MN | — | Positive deflection | Positive deflection | Positive deflection |
| Primary #1 | — | — | — | — |
| Primary #2 | — | — | — | — |
| Primary #3 | — | — | — | Positive |
| Primary #4 | — | — | — | — |

Mixed VVenv elicit a higher quality of HIV-1 specific antibodies than single VVenv. The results of ELISA and neutralization assays are summarized in Table 4 listing those chimps whose sera yielded the higher responses in the seven tests described above. As may be noted from the table, chimps 3 and 4 scored positively in a composite of five out of seven tests, while chimps 1 and 2 scored positively in only three out of seven. This result may reflect a higher quality of antibodies elicited by Poly Env as compared to single Env vaccines.

TABLE 4

Summary of ELISA and neutralization assays

| Assay | Higher responses among chimps given a single VV | Higher responses among chimps given mixed VV |
| --- | --- | --- |
| Abbott (IIIB-gp41)-ELISA #1 | | Chimp 3 and Chimp 4 |
| MNgp160BAC ELISA #2 | | Chimp 3 |
| IIIB-gp120-BAC-ELISA #3 | Chimp 2 | |
| LaI-gp120-CHO-ELISA #4 | | Chimp 3 |
| III b Virus lysate ELISA #5 | Chimp 1 and Chimp 2 | Chimp 3 and Chimp 4 |
| Lab Isolate-neutralization (deflection) | Chimp 2 | Chimp 3 and 4 |
| Primary Isolate-neutralization | | Chimp 4 |

Discussion

Experiments described in this Example were designed to test the safety of a vaccinia virus-based HIV-1 vaccine and to compare the efficacy of priming with envelope cocktails and single envelope vaccines. Results demonstrated first, that vaccinia virus could be used as an immunogen without inducing an open lesion, and secondly, that a great breadth of HIV-1-specific activity could be elicited with the envelope cocktail.

The chimpanzee model allowed us to examine the safety of PolyEnv in primates. We were particularly interested to determine the extent of open lesion formation, as VV inoculations could pose a threat of live virus transfer to unimmunized individuals. In the case of HIV, this is a serious concern in that an AIDS patient may not be capable of blocking the VV infection. To address this concern, we tested the use of subcutaneous vaccinations in chimpanzees, questioning whether an open lesion could be avoided. Indeed, only two of the four chimpanzees demonstrated open lesions. Similar results were observed when subcutaneous inoculations of the NYCDH vaccinia virus stock were used in clinical trials of the small pox vaccine [Connor et al., *Journal of Infectious diseases* 135:167–175 (1977); Benenson et al., *Journal of Infectious diseases* 135:135–144 (1977)].

It is likely that with additional attention to the injection procedure and follow-up care of the injection site, open lesions may be avoided in all cases. These results demonstrate that safety issues need not preclude the use of vaccinia virus as an HIV-1 vaccine vector.

Envelope cocktails have been tested in mouse (Example 2) and rabbit experiments. In the mouse experiments, anti-HIV antibodies were monitored after a single injection of VVenv, while in rabbits, VVenv were used to boost responses elicited with DNA-based. Experiments indicated that HIV-l specific antibodies could be elicited or boosted with VVenv, and that primary isolates could be neutralized by the antibody response. To examine the potential of mixed VVenv (PolyEnv), chimpanzees were divided into two groups. The first two chimps received only one VVenv while chimps 3 and 4 received cocktails composed of a total of thirty different VVenv.

After having received vaccinia virus immunizations, all four chimps were given a booster with a single gp120/gp41 protein mix in alum. The sera from each of the four chimpanzees were tested in five different ELISAs, each utilizing a different fragment and/or configuration of Env. Interestingly, chimps 1 and 2 as a composite responded strongly in only one of these ELISAs, whereas the sera from chimps 3 and 4 as a composite responded strongly in 4 such assays. As each assay measured only a fraction of the HIV-1 specific antibody in each animal, results likely reflected the superior breadth of antibody binding activities elicited by the mixed vaccine.

Neutralization assays were also performed both against laboratory and primary isolates. Interestingly, a positive response against a primary isolate was noted in chimp 4, even though the primary isolate had not been specifically represented in the vaccine mix. Again, these results demonstrated a greater breadth of antibodies elicited by the PolyEnv vaccine cocktail. Increase in the antigen complexity of a vaccine might be expected to lead to an increased diversity of lymphocyte and respective antibody responses.

The demonstration that neutralizing antibodies can be elicited against a primary isolate that is not represented in the vaccine demonstrates that linearly distinct proteins share conformational structures. This notion is also demonstrated by the immune responses of HIV-1-infected patients, in that any two individuals who are exposed to a myriad of mutually exclusive viruses, are generally protected from superinfection when cross-exposure occurs. The use of PolyEnv represents a first attempt in a chimpanzee system to mimic the situation in HIV-1 patients. That is, neutralizing antibodies are elicited with a large array of, rather than a single, Env protein.

In summary, we have tested an VV-based HIV-1 vaccine cocktail called PolyEnv in a chimpanzee model. This Example has demonstrated:

1) VV could be used as a vaccine without inducing an open skin lesion;

2) a great breadth of HIV-1 specific antibody activities could be elicited with this vaccine; and 3) a cocktail of Env constructs (PolyEnv) yielded a superior quality of HIV-specific antibodies as compared to a single Env construct.

Vaccinia virus has long been known to be a potent vaccine, both in wildtype form and recombinant form. The strength of VV lies in its power to recruit both the B- and cytotoxic T-lymphocyte compartments of the immune response. VV has comprised the only vaccine capable of eradicating a disease (smallpox) from the human population. The data in this Example indicate that recombinant VV vectors will contribute to the future control of HIV-1.

Example 4
Preparation of a Bi-Functional Plasmid

DNA vaccines have been shown to elicit strong antibody and CTL responses in several, distinct systems (influenza, HIV-1, etc.). DNA-based influenza and HIV-1 vaccines are already in clinical trials with healthy adult volunteers. Vaccinia virus also serves as a strong base for vaccination programs. In fact, vaccinia virus has been the only vaccine able to eradicate a disease (small pox) from the human population. Numerous recombinant vaccinia viruses have elicited protective immune responses as demonstrated in animal studies. The data shown above demonstrate the effectiveness of a polyenv vaccine, and of combining vaccination strategies, e.g., DNA vaccines and viral vaccines.

A bi-functional plasmid that can act both as a DNA vaccine and a VV recombinant vector is constructed. FIG. 7 shows a map of this plasmid, which includes a CMV promoter for expression in mammalian cells, and vaccinia early and late promoters for preparation of recombinant vaccinia. The direct injection of purified plasmid DNA would be used to elicit immune responses against an HIV env protein in test subjects. The plasmid would also be used to prepare and test live, recombinant vaccinia viruses as HIV env protein immunization vehicles.

Subjects could potentially be vaccinated with a multi-tiered regimen, comprised both of DNA vaccination(s) and recombinant vaccinia virus immunization(s), given in any order, in single or multiple injections and/or in conjunction with additional vaccine vehicles.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

REFERENCE LIST

Ausubel et al., eds, *Current Protocols in Molecular Biology*, Greene Publishing Assoc., New York, N.Y. (1987, 1988, 1989, 1990, 1991, 1992, 1993, 1994, 1995)

Avery's *Drug Treatment: Principles and Practice of Clinical Pharmacology and Therapeutics*, Third Edition, ADIS Press, LTD., Williams and Wilkins, Baltimore, Md. (1987)

Belshe, R. B. et al., *J. Am. Med. Assoc.* 272:431–431 (1994)

Berkow et al., eds., *The Merck Manual*, Fifteenth Edition, Merck and Co., Rahway, N.J. (1987)

Bimboim, H. C. and Doly, J., *Nucleic Acids Res.* 7:1513–1523 (1979)

Buck, C., and Paulino, M. S., eds., *American Type Culture Collection Catalogue of Animal Viruses and Antisera, Chlamydiae and Rickettsiae*, 6th Ed., American Type Culture Collection, Rockville, Md. (1990)

Burns, D. P. W. and Desrosiers, R. C., *Cur. Topics Microbiol. Immunol.* 188:185–219 (1994)

Chakrabarti, S. et al., *Mol. Cell. Biol.* 5:3403–3409 (1985)

Cooney et al., *Proc. Natl. Acad. Sci. USA* 90:1882–1886 (1993)

Creighton, T. E., *Proteins: Structure and Molecular Properties*, W. H. Freeman & Co., San Francisco, Calif. (1983)

DeVita Jr., V. T. et al., *AIDS, Etiology, Diagnosis, Treatment and Prevention,* 3rd edition, J. B. Lippincott Co., Philadelphia, Pa. (1992)

D'Honcht, *Vaccine* 10 Suppl.:548–52 (1992)

Dorozynski and Anderson, *Science* 252:501–502 (1991)

Ebadi, *Pharmacology*, Little, Brown and Co., Boston, Mass. (1985)

Eichberg, *Int. Conf. AIDS* 7:88 (1991)

Embretson, J. et al., *Nature* 362:359–362 (1993)

Enami et al., *J. Virol.* 65:2711–2713 (1991)

Enami et al., *Proc. Natl. Acad. Sci. USA* 87:3802–3805 (1990)

Fauci, *Science* 264:1072–1073 (1994)

Goodman et al., eds., *Goodman and Gilman's The Pharmacological Basis of Therapeutics*, Eighth Edition, Pergamon Press, Inc., Elmsford, N.Y. (1990)

Gorse, *AIDS Res. Hum. Retrovir.* 10 (Suppl. 2):141–143 (1994)
Gribskov and Burgess, *Nucl. Acids Res.* 14:6745 (1986)
Graham et al., *J. Infect. Dis.* 166:244–252 (1992); *J. Infect. Dis.* 167:533–537 (1993)
Grundwald-Bearch et al., *J. Cancer Res. Clin. Oncol.* 117:561–567 (1991)
Hallenberger et al., *Virology* 193:510–514 (1993)
Hay, R., et al., eds., *American Type Culture Collection Catalogue of Cell Lines and Hybridomas,* 7th Ed., American Type Culture Collection, Rockville, Md. (1992)
Hirsch, M. S., and Curran, J. "Human immunodeficiency viruses, biology and medical aspects," in *Virology*, Fields and Knipe, eds., Raven Press, Ltd., New York, N.Y. (1990), pp 1545–1570
Hu et al., *Nature* 328:721–723 (1987)
Ish-Horowicz, D. and Burke, J. F., *Nucleic Acids Res.* 9:2989–2998 (1981)
Ito et al., *J. Virol.* 65:5491–5498 (1991)
Ito et al., *Cancer Res.* 50:6915–6918 (1990)
Javaherian, K. et al., *Proc. Natl. Acad. Sci. (USA)* 86:6768–6772 (1989)
Katzung, ed., *Basic and Clinical Pharmacology*, Fifth Edition, Appleton and Lange, Norwalk, Conn. (1992)
Keefer et al., *AIDS Res. Hum. Retrovir.* 10 (Suppl. 2):S139–143 (1994)
Kieny et al., *Int. Conf. AIDS* 5:541 (1989)
Kilpatrick et al. *J. Biol. Chem.* 262:116–121 (1987)
Luytjes et al., *Cell* 59:1107–1113 (1989)
Mackett, M. et al., *Proc. Natl. Acad. Sci. (USA)* 79:7415–7419 (1982)
Mazzara, G. P. et al., *Methods in Enz.* 217:557–581 (1993)
McElrath et al., *J. Infect. Dis.* 169:4147 (1994)
Needleman and Wunsch, *J. Mol. Biol.* 48:443 (1970)
Osol, A., ed., *Remington's Pharmaceutical Sciences*, Mack Publishing Co., Easton, Pa. (1980), pp. 1324–1341
Panicali, D., and Paoletti, E., *Proc. Natl. Acad. Sci. (USA)* 79:4927–4931 (1982)
Pantaleo, G. et al., *Nature* 362:355–358 (1993)
Rhim, J. S. et al., *Int. J. Cancer* 15:23–29 (1975)
Richman, *AIDs Res. Hum. Retroviruses* 8: 1065–1071 (1992);
Richman, *Annu Rev Pharmacol Toxico* 33: 149–164 (1993);
Richman, *Antimicrob Agents Chemother* 37: 1207–1213 (1993);
Richman, *AIDs Res. Hum. Retroviruses* 10: 901 (1994)
Richmond and McKinney, eds, *Biosafety in microbiological and biomedical laboratories,* 3rd Edition, U.S. Dept. of Health & Human Services, Washington D.C. (1993)
Sambrook, J. et al., *Molecular Cloning: A Laboratory Manual,* Second Edition, Cold Spring Harbor Laboratory Press, Cold Spring Harbor, N.Y. (1989)
Schulz, G. E. et al., *Principles of Protein Structure,* Springer-Verlag, New York, N.Y. (1978)
Schwartz and Dayhoff, eds., *Atlas of Protein Sequence and Structure,* National Biomedical Research Foundation, [Washington, D.C. ?-wp] (1979), pp. 353–358
Selenka et al., *Arch. Hyg. Bakteriol.* 153:244–253 (1969)
Smith and Waterman, *Adv. Appl. Math.* 2:482 (1981)
Starcich et al., *Cell* 45:637 (1986)
Towbin, H. et al., *Proc. Natl. Acad. Sci. (USA)* 76:4350 (1979)
United States Biochemical, *Sequenase Version 2.0—DNA Sequencing Kit,* Ninth Edition, Amersham Life Science, Inc., Boise, Id. (1994)
Weir et al., *Proc. Natl. Acad. Sci. U.S.A.* 79:1210–1214 (1982)
Wellis et al., *J. Immunol.* 99:1134–9 (1967)
Wong-Staal, F., "Human immunodeficiency viruses and their replication," in *Virology*, Fields and Knipe, eds., Raven Press, Ltd., New York, N.Y. (1990), pp 1529–1543
Wrin et al., *J. Acquir. Immune Defic. Syndr.* 7:211–219 (1994)
Wu et al., *Prog. Nucl. Acid. Res. Molec. Biol.* 21:101–141 (1978)
Zagury et al., *Nature* 332:728–731 (1988)

What is claimed is:

1. A bi-functional plasmid that can serve as a DNA vaccine and a recombinant virus vector, comprising a heterologous gene and/or an insertion site for a heterologous gene under control of both an animal expression control sequence, and a viral expression control sequence.

2. The bi-functional plasmid of claim 1 wherein the animal expression control sequence is a cytomegalovirus immediate early (CMV) promoter.

3. The bi-functional plasmid of claim 1 comprising a heterologous gene, wherein the heterologous gene is an env variant (EV) nucleic acid encoding both variable and constant regions of an envelope protein variant of an HIV envelope protein.

4. The bi-functional plasmid of claim 2 comprising a heterologous gene, wherein the heterologous gene is an env variant (EV) nucleic acid encoding both variable and constant regions of an envelope protein variant of an HIV envelope protein.

5. The bi-functional plasmid of claim 1 wherein the virus expression control sequence is a vaccinia virus early promoter.

6. The bi-functional plasmid of claim 5 comprising a heterologous gene, wherein the heterologous gene is an env variant (EV) nucleic acid encoding both variable and constant regions of an envelope protein variant of an HIV envelope protein.

7. The bi-functional plasmid of claim 1 wherein the virus expression control sequence is a vaccinia virus late promoter.

8. The bi-functional plasmid of claim 7 comprising a heterologous gene, wherein the heterologous gene is an env variant (EV) nucleic acid encoding both variable and constant regions of an envelope protein variant of an HIV envelope protein.

9. The bi-functional plasmid of claim 1 wherein the virus expression control sequence is both a vaccinia virus early promoter and a vaccinia virus late promoter.

10. The bi-functional plasmid of claim 9 comprising a heterologous gene, wherein the heterologous gene is an env variant (EV) nucleic acid encoding both variable and constant regions of an envelope protein variant of an HIV envelope protein.

11. The bi-functional plasmid of claim 2 wherein the virus expression control sequence is a vaccinia virus early promoter.

12. The bi-functional plasmid of claim 11 comprising a heterologous gene, wherein the heterologous gene is an env variant (EV) nucleic acid encoding both variable and constant regions of an envelope protein variant of an HIV envelope protein.

13. The bi-functional plasmid of claim 2 wherein the virus expression control sequence is a vaccinia virus late promoter.

14. The bi-functional plasmid of claim 13 comprising a heterologous gene, wherein the heterologous gene is an env variant (EV) nucleic acid encoding both variable and constant regions of an envelope protein variant of an HIV envelope protein.

15. The bi-functional plasmid of claim 2 wherein the virus expression control sequence is both a vaccinia virus early promoter and a vaccinia virus late promoter.

16. The bi-functional plasmid of claim 15 comprising a heterologous gene, wherein the heterologous gene is an env variant (EV) nucleic acid encoding both variable and constant regions of an envelope protein variant of an HIV envelope protein.

17. An immunogenic composition that can elicit an immune response to more than one but not necessarily all of the env variants contained in the composition, comprising at least 4 different bi-functional plasmids, each encoding a different envelope protein variant (EPV) of a human immunodeficiency virus (HIV) envelope protein, wherein a) the EPV contains both variable and constant regions;
b) the immunogenic composition is capable of eliciting at least one of a cellular and a humoral immune response in a mammal against an HIV strain; and
c) wherein the expression of each of said different EPVs is under the control of both an animal expression control sequence, and a viral expression control sequence.

18. The bi-functional plasmid of claim 17 wherein the animal expression control sequence is a cytomegalovirus immediate early (CMV) promoter.

19. The bi-functional plasmid of claim 18 wherein the virus expression control sequence is a vaccinia virus early promoter.

20. The bi-functional plasmid of claim 18 wherein the virus expression control sequence is a vaccinia virus late promoter.

21. The bi-functional plasmid of claim 18 wherein the virus expression control sequence is both a vaccinia virus early promoter and a vaccinia virus late promoter.

22. The bi-functional plasmid of claim 17 wherein the virus expression control sequence is a vaccinia virus early promoter.

23. The bi-functional plasmid of claim 17 wherein the virus expression control sequence is a vaccinia virus late promoter.

24. The bi-functional plasmid of claim 17 wherein the virus expression control sequence is both a vaccinia virus early promoter and a vaccinia virus late promoter.

* * * * *